(12) United States Patent
Kim et al.

(10) Patent No.: US 9,744,083 B2
(45) Date of Patent: Aug. 29, 2017

(54) APERTURED OUTER COVER FOR ABSORBENT ARTICLES

(71) Applicant: Kimberly-Clark Worldwide, Inc., Neenah, WI (US)

(72) Inventors: Kyungnak Kim, Seongnam-si (KR); JinHo Ryu, Yongin-si (KR); Seungkeun Park, Yongin-si (KR); JinHee Lee, Anyang (KR); EoYeon Hwang, Yongin-si (KR); SooYong Cho, GyeongGi (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 127 days.

(21) Appl. No.: 14/046,541

(22) Filed: Oct. 4, 2013

(65) Prior Publication Data
US 2015/0099086 A1 Apr. 9, 2015

(51) Int. Cl.
*A61F 13/514* (2006.01)
*B32B 3/24* (2006.01)
(Continued)

(52) U.S. Cl.
CPC .... *A61F 13/5146* (2013.01); *A61F 13/15707* (2013.01); *A61F 13/5148* (2013.01); *A61F 13/51462* (2013.01); *A61F 13/51474* (2013.01); *A61F 13/51476* (2013.01); *B32B 5/26* (2013.01); *B32B 7/045* (2013.01); *A61F 13/15699* (2013.01); *A61F 13/51456* (2013.01);
(Continued)

(58) Field of Classification Search
CPC .............. A61F 13/5146; A61F 13/5148; A61F 2013/51486; A61F 2013/5149
See application file for complete search history.

(56) References Cited

U.S. PATENT DOCUMENTS 2,851,390 A * 9/1958 Chavannes ........ A41D 31/0016
156/252
3,787,955 A * 1/1974 Wilson .................. A47J 36/022
156/253
(Continued)

FOREIGN PATENT DOCUMENTS

CN 202908956 U * 5/2013
DE 19523497 A1 * 1/1997 ....... A61F 13/51476
(Continued)

OTHER PUBLICATIONS

Machine Translation of JP 2002325800 A, Nov. 2002.*
(Continued)

*Primary Examiner* — Jeff Vonch
(74) *Attorney, Agent, or Firm* — Armstrong Teasdale LLP

(57) ABSTRACT

An outer cover for an absorbent article includes a nonwoven component having a plurality of apertures formed therein and a film bonded to the apertured nonwoven component. The apertures in the nonwoven component are formed by needling prior to the film being bonded to the nonwoven component. A method of making the outer cover includes feeding a web of nonwoven material to a needling station, needling the web of nonwoven material to form a plurality of apertures therein to define an apertured web of nonwoven material, and bonding the apertured web of nonwoven material to a film.

16 Claims, 11 Drawing Sheets

(51) Int. Cl.
*B32B 3/28* (2006.01)
*B32B 3/30* (2006.01)
*B32B 7/12* (2006.01)
*B32B 27/12* (2006.01)
*B32B 38/04* (2006.01)
*B32B 7/04* (2006.01)
*B32B 5/26* (2006.01)
*B32B 5/02* (2006.01)
*B32B 3/26* (2006.01)
*A61F 13/15* (2006.01)

(52) U.S. Cl.
CPC ... *A61F 13/51458* (2013.01); *A61F 13/51478* (2013.01); *A61F 13/51498* (2013.01); *A61F 2013/51411* (2013.01); *A61F 2013/51447* (2013.01); *A61F 2013/51452* (2013.01); *B32B 3/266* (2013.01); *B32B 3/28* (2013.01); *B32B 3/30* (2013.01); *B32B 5/022* (2013.01); *B32B 7/12* (2013.01); *B32B 27/12* (2013.01); *B32B 2038/047* (2013.01); *B32B 2250/02* (2013.01); *B32B 2307/30* (2013.01); *B32B 2307/50* (2013.01); *Y10T 156/1025* (2015.01); *Y10T 156/1056* (2015.01); *Y10T 156/1062* (2015.01); *Y10T 428/23* (2015.01); *Y10T 428/24281* (2015.01); *Y10T 428/24322* (2015.01); *Y10T 428/24331* (2015.01); *Y10T 428/24661* (2015.01); *Y10T 428/24826* (2015.01); *Y10T 442/674* (2015.04)

(56) References Cited

U.S. PATENT DOCUMENTS

| | | | |
|---|---|---|---|
| 3,881,489 A * | 5/1975 | Hartwell | A61F 13/5146 428/137 |
| 3,886,941 A * | 6/1975 | Duane | A61F 13/512 604/366 |
| 3,929,135 A * | 12/1975 | Thompson | 604/385.08 |
| 3,989,867 A * | 11/1976 | Sisson | A61F 13/5146 428/132 |
| 4,306,559 A * | 12/1981 | Nishizawa | A61F 13/5146 604/366 |
| 4,341,216 A * | 7/1982 | Obenour | 604/370 |
| 4,341,217 A * | 7/1982 | Ferguson | A61F 13/512 604/370 |
| 4,386,932 A * | 6/1983 | Pitts | A61F 13/51401 604/383 |
| 4,681,793 A | 7/1987 | Linman et al. | |
| 4,713,068 A | 12/1987 | Wang et al. | |
| 4,725,473 A * | 2/1988 | Van Gompel | A61F 13/51464 156/209 |
| 4,741,941 A * | 5/1988 | Englebert | A47L 13/16 15/209.1 |
| 4,842,596 A | 6/1989 | Kielpikowski et al. | |
| 5,387,209 A * | 2/1995 | Yamamoto | A61F 13/512 604/358 |
| 5,449,352 A * | 9/1995 | Nishino | A61F 13/15731 604/358 |
| 5,460,624 A | 10/1995 | Ahr et al. | |
| 5,571,096 A | 11/1996 | Dobrin et al. | |
| 5,575,874 A * | 11/1996 | Griesbach, III | A61F 13/15658 156/167 |
| 5,695,868 A * | 12/1997 | McCormack | B32B 5/24 428/516 |
| 5,718,698 A | 2/1998 | Dobrin et al. | |
| 5,762,643 A * | 6/1998 | Ray | A61F 13/15699 428/132 |
| 5,843,056 A | 12/1998 | Good et al. | |
| 5,897,541 A * | 4/1999 | Uitenbroek | A61F 13/15203 604/358 |
| 5,990,376 A * | 11/1999 | Inoue | A61F 13/5148 604/358 |
| 6,045,900 A | 4/2000 | Haffner et al. | |
| 6,075,179 A | 6/2000 | McCormack et al. | |
| 6,140,551 A * | 10/2000 | Niemeyer | A61F 13/15203 604/358 |
| 6,168,849 B1 * | 1/2001 | Braverman | A61F 13/15731 156/148 |
| 6,177,607 B1 | 1/2001 | Blaney et al. | |
| 6,316,687 B1 | 11/2001 | Davis et al. | |
| 6,369,292 B1 | 4/2002 | Strack et al. | |
| 6,429,352 B1 | 8/2002 | Herrlein et al. | |
| 6,583,331 B1 | 6/2003 | McCormack et al. | |
| 6,589,632 B1 * | 7/2003 | Sugimura | A61F 13/5146 428/131 |
| 6,624,341 B1 * | 9/2003 | Depner | A61F 13/5146 604/367 |
| 6,849,319 B2 * | 2/2005 | Cree | A61F 13/512 428/137 |
| 2001/0029141 A1 * | 10/2001 | Mizutani | A61F 13/512 442/327 |
| 2001/0041248 A1 * | 11/2001 | Matsushita | A61F 13/15203 428/200 |
| 2002/0016122 A1 * | 2/2002 | Curro | A47L 1/15 442/381 |
| 2002/0123729 A1 | 9/2002 | Bewick-Sonntag et al. | |
| 2002/0147435 A1 | 10/2002 | Coles et al. | |
| 2002/0193032 A1 * | 12/2002 | Newkirk | A61F 13/49453 442/401 |
| 2002/0193774 A1 * | 12/2002 | Otsubo | A61F 13/51464 604/385.22 |
| 2003/0026945 A1 * | 2/2003 | Lasko | A61F 13/15731 428/131 |
| 2003/0091797 A1 * | 5/2003 | Sugimura | A61F 13/5146 428/179 |
| 2003/0124308 A1 * | 7/2003 | Cree | A61F 13/5146 428/137 |
| 2003/0124311 A1 * | 7/2003 | Cree | A61F 13/5122 428/138 |
| 2004/0127873 A1 | 7/2004 | Varona et al. | |
| 2005/0095941 A1 * | 5/2005 | Coronado | A61F 13/15699 442/327 |
| 2005/0261650 A1 | 11/2005 | Damaghi et al. | |
| 2006/0057924 A1 * | 3/2006 | Cheng | B32B 5/022 442/394 |
| 2006/0058772 A1 | 3/2006 | Karami | |
| 2006/0087053 A1 * | 4/2006 | O'Donnell | B26F 1/18 264/156 |
| 2006/0128245 A1 * | 6/2006 | Muth | B26F 1/24 442/327 |
| 2006/0142719 A1 | 6/2006 | Vogt et al. | |
| 2006/0286353 A1 * | 12/2006 | Stridfeld | A61F 13/51458 428/174 |
| 2007/0298667 A1 * | 12/2007 | Noda | D04H 1/465 442/50 |
| 2008/0045917 A1 | 2/2008 | Autran et al. | |
| 2008/0227356 A1 * | 9/2008 | Poruthoor | C09D 11/03 442/394 |
| 2010/0114048 A1 | 5/2010 | Bishop et al. | |
| 2010/0179495 A1 | 7/2010 | Roe | |
| 2010/0201024 A1 * | 8/2010 | Gibson | B26F 1/20 264/156 |
| 2010/0280478 A1 | 11/2010 | Lavon et al. | |
| 2012/0177886 A1 * | 7/2012 | Kanya | A61F 13/51476 428/156 |
| 2012/0179125 A1 * | 7/2012 | Kanya | A61F 13/51476 604/366 |
| 2013/0253461 A1 | 9/2013 | Xu et al. | |
| 2014/0322497 A1 * | 10/2014 | Kelsey | C09J 7/04 428/175 |

FOREIGN PATENT DOCUMENTS

| | | | | |
|---|---|---|---|---|
| DE | 19826455 A1 * | 9/1999 | | A61F 13/023 |
| EP | 474123 A1 * | 3/1992 | | |
| EP | 710471 A1 * | 5/1996 | | |
| EP | 738505 A1 * | 10/1996 | | |
| EP | 1040799 A1 * | 10/2000 | | A61F 13/51462 |
| EP | 1040807 A1 | 10/2000 | | |

(56) References Cited

FOREIGN PATENT DOCUMENTS

| EP | 1064900 A1 | * | 1/2001 | ......... A61F 13/5148 |
|----|------------|---|--------|------------------------|
| EP | 1873289 A1 | * | 1/2008 | ........... D04H 1/4266 |
| JP | 60027530 A | * | 2/1985 | |
| JP | 06330443 A | * | 11/1994 | |
| JP | 11113954 A | * | 4/1999 | |
| JP | 2002325800 A | * | 11/2002 | ............. A61F 13/49 |
| JP | 2003025471 A | * | 1/2003 | |
| JP | 2004081669 A | * | 3/2004 | |
| JP | 2004114697 A | * | 4/2004 | |
| JP | 2005246811 A | * | 9/2005 | |
| JP | 2005246812 A | * | 9/2005 | |
| JP | 2007105184 A | * | 4/2007 | |
| JP | 2011078545 A | * | 4/2011 | |
| JP | 2014121494 A | * | 7/2014 | |
| KR | 20010011672 A | * | 2/2001 | |
| KR | 20130103922 A | * | 9/2013 | |
| WO | WO 9424354 A1 | * | 10/1994 | ....... A61F 13/15731 |
| WO | WO 2005011936 A1 | * | 2/2005 | ................ B26F 1/24 |

OTHER PUBLICATIONS

Machine Translation of CN 202908956 U, May 2013.*
Machine Translation of WO 9424354 A1, Oct. 1994.*
Notification of Transmittal of the International Search Report and the Written Opinion of the International Searching Authority for International Application No. PCT/IB2014/063942, dated Mar. 17, 2015; 13 pages.
Supplementary European Search Report issued in EP 14850512 dated May 10, 2017, 8 pages.

* cited by examiner

APERTURED OUTER COVER FOR ABSORBENT ARTICLES

FIELD

The field of the invention relates generally to outer covers for absorbent articles and more specifically to an outer cover comprising an apertured nonwoven configured to improve softness, heighten the user's awareness of the outer cover's breathability, and reduce dampness.

BACKGROUND

Absorbent articles, such as diapers, incontinence garments, training pants, sanitary napkins, panty liners, and the like are well known in the art. These articles, which are often disposable, are capable of absorbing and retaining fluids and other bodily discharges. These absorbent articles typically have an outer cover with a liquid impermeable plastic film, such as polypropylene and/or polyethylene, to prevent liquid discharged by a wearer from leaking from the article.

Some known absorbent articles having liquid impermeable outer covers include a film that is impervious to water vapor as well as liquid. Because the outer cover is impermeable to both liquids and water vapor, the absorbent article often feels hot and clammy to the wearer especially after a bodily discharge. Furthermore, this lack of permeability to both liquid and water vapor may cause irritation to the skin of the wearer. In addition to concerns over skin wellness, the liquid impermeable plastic films often lacked the aesthetic and tactile qualities desired in absorbent articles.

Other known outer covers for absorbent articles are "breathable". Such outer covers, which are typically laminates of several different types of material, are substantially impervious to liquids but are "breathable" in the sense that water vapor can pass through the outer cover. Breathable outer covers have become increasingly popular and are highly commercialized in absorbent articles.

While often providing a more skin friendly product, breathable liquid-impervious outer covers often suffer from outer cover dampness. That is, many absorbent articles having such an outer cover develop a wet or damp feel on the outer surface of the outer cover after fluid is discharged by the wearer and absorbed by the article. This unpleasant wet feeling is not typically due to permeation of liquid through the liquid-impermeable cover or leakage from the article but rather by the condensation of water vapor on the outer cover as a result of relatively warm vapor passing through the outer cover, cooling, and condensing on the outer cover.

It is often difficult for users (e.g., wearers, caregivers) of absorbent articles to readily determine if the article they are using has a non-breathable or breathable outer cover. That is, the articles having breathable outer covers are often not readily discernible from articles having non-breathable outer covers. As mentioned above, breathable outer covers often provide a skin healthier product from the wearer's perspective as compared to non-breathable outer covers.

Thus, there exists a need for an absorbent article having sufficient water vapor permeation to remain a healthy and comfortable product for the wearer but that inhibits the outer cover from developing a wet or damp feel. Moreover, there exists a need for such an absorbent article configured to heighten the awareness of the outer cover's breathability to the user. There also exists a need for such an absorbent article having such an outer cover that is soft.

BRIEF DESCRIPTION

In one aspect, an outer cover for an absorbent article generally comprises a nonwoven component having a plurality of apertures formed therein and a film bonded to the apertured nonwoven component. The apertures in the nonwoven component are formed by needling prior to the film being bonded to the nonwoven component.

In another aspect, an outer cover for an absorbent article generally comprises a nonwoven component defining a plurality of apertures formed therein and a film adhesively bonded to the apertured nonwoven component. The nonwoven component defines a plurality of domed areas extending away from the film. The nonwoven component is adhesively bonded to the film at locations adjacent the apertures.

In yet another aspect, a method of making an outer cover for an absorbent article generally comprises feeding a web of nonwoven material to a needling station. The web of nonwoven material is needled at the needling station to form a plurality of apertures therein to define an apertured web of nonwoven material. The apertured web of nonwoven material is adhesively bonded to a film.

DETAILED DESCRIPTION OF THE DRAWINGS

With reference now to the drawings, FIGS. 1-4 illustrate one suitable embodiment of an absorbent article of the present disclosure in the form of a diaper, indicated generally at 10. While the present disclosure will be made in the context of a diaper, it should be understood that the present disclosure is applicable to other absorbent articles, such as, for example, adult incontinence garments, children's training pants, diaper pants, swim diapers, feminine care articles (e.g., sanitary napkins, panty liners), wound dressings, bandages, sterilization wraps, surgical gowns, drapes, wipes, protective apparel and the like.

In one suitable embodiment, the diaper 10 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 10 (or more broadly, the absorbent article) can be reusable. That is, the absorbent article can be intended for multiple uses without departing from some aspects of this disclosure.

Figure 1:
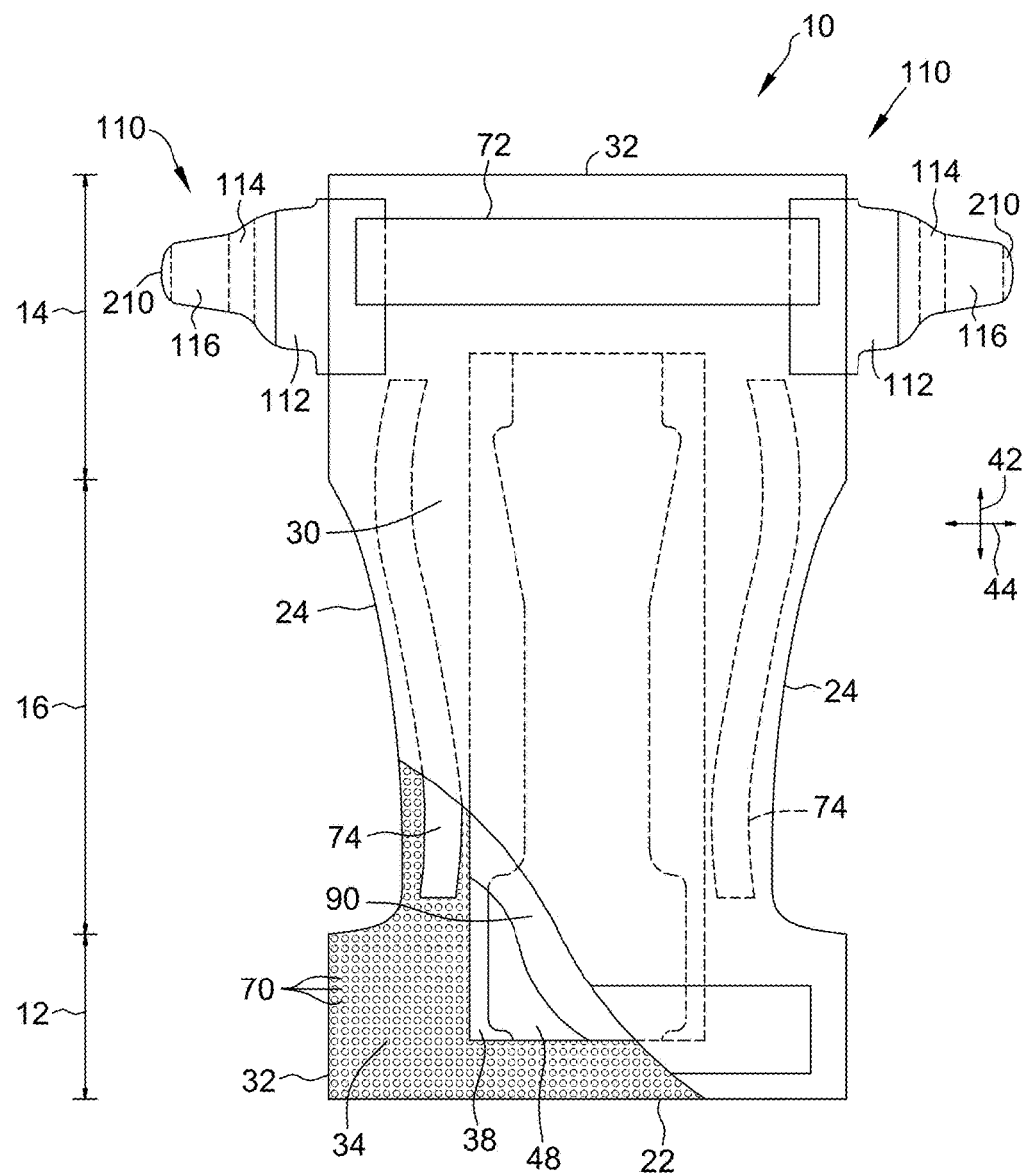
FIG. 1 is a top plan view of an absorbent article according to one embodiment of the present disclosure in the form of a diaper, the diaper being illustrated in an unfolded and laid flat condition to show an inner surface of the diaper which faces towards the wearer when the diaper is worn.
Figure 2:
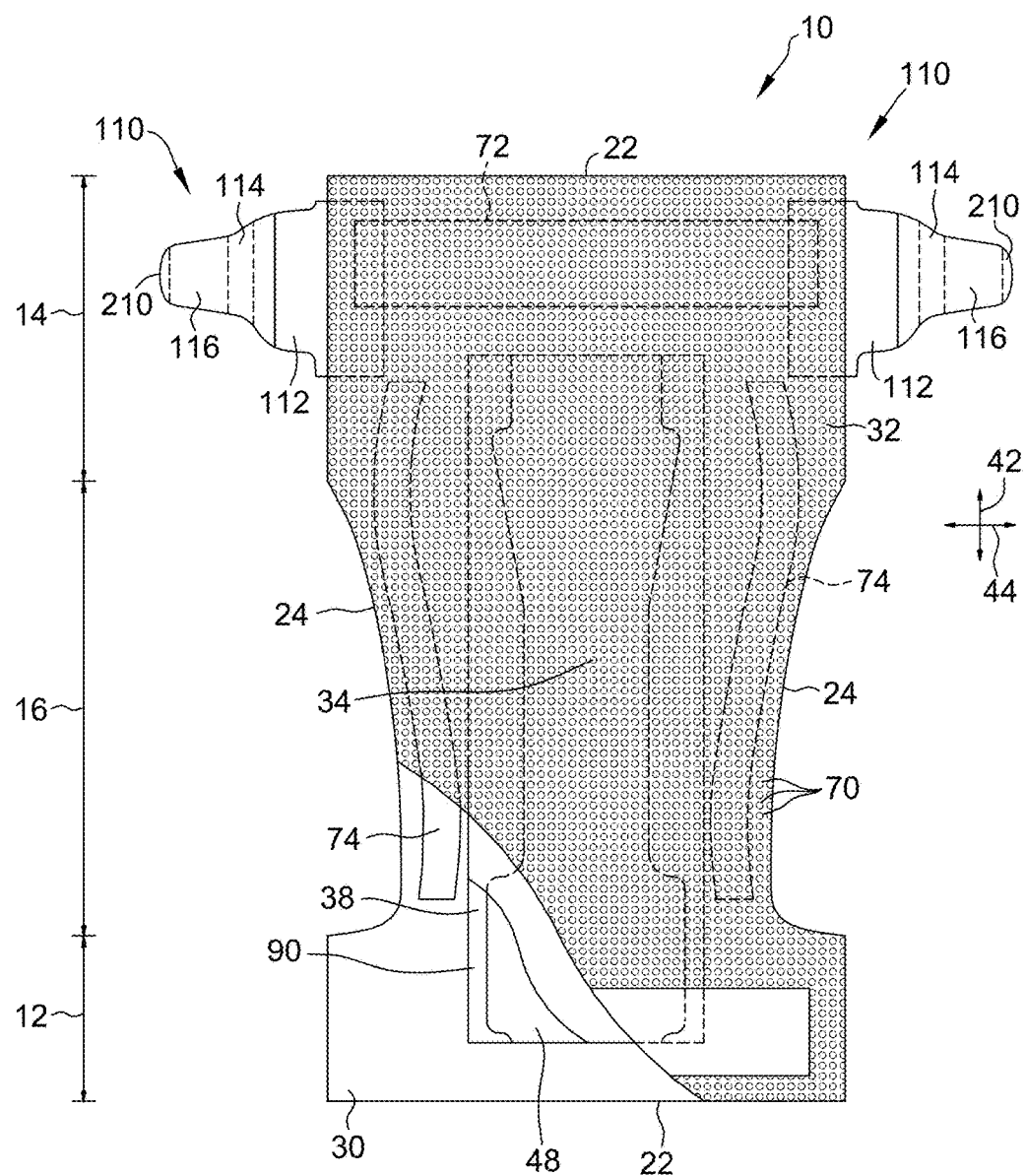
FIG. 2 is a bottom plan view of the diaper in an unfolded and laid flat condition to show an outer surface of the diaper which faces away from the wearer when the diaper is worn.

FIG. 1 illustrates the diaper 10 in an unfolded and laid flat condition to show an inner surface of the diaper which faces the wearer when the diaper is worn. FIG. 2, on the other hand, illustrates the diaper 10 in an unfolded and laid flat condition to show an outer surface of the diaper which faces away from the wearer when the diaper is worn. Portions of the diaper 10 are cut away in FIGS. 1 and 2 to illustrate internal components of the diaper.

With reference still to FIGS. 1 and 2, the diaper 10 has a longitudinal direction 42 and a lateral direction 44. In the longitudinal direction 42, the diaper 10 defines a front portion 14, a back portion 16, and a crotch portion 18 extending between and connecting the front portion 14 and the back portion 16. The front portion 14 of the diaper 10 is intended to be generally located on the front of a wearer during use; the back portion 16 is intended to be generally located at the back of the wearer during use; and the crotch portion 18 is intended to be generally located between the legs of the wearer during use.

In the illustrated embodiment, both the back portion 16 and the front portion 14 include a straight waist (or end) edge 22. As used herein, a "straight edge" refers to an edge that is substantially free from curves, bends, angles, notches or irregularities. It is understood, however, that the back and/or front waist edge 22 can be cut in any suitable shape as is known in the art (e.g., arcuate). As seen in FIGS. 1 and 2, the diaper 10 has opposite longitudinal side edge 24 that extend between the back and front waist edges 22. In the illustrated embodiment, each of the side edges 24 includes a nonlinear portion that defines at least part of a leg opening during wear of the diaper 10. It is understood that the side edges 24 can have any suitable shape including straight.

As seen in FIGS. 1 and 2, the diaper 10 includes a bodyside liner 30, an outer cover 32 and an absorbent structure 48 located between the bodyside liner and the outer cover. The bodyside liner 30 of the diaper 10, as illustrated in FIG. 1, defines the body facing surface of the diaper. Thus, the bodyside liner 30 is intended to be adjacent to and in directed contact with the body of the wearer when the wearer dons the diaper 10. As a result, the bodyside liner 30 is suitably compliant, soft feeling and nonirritating to the wearer's skin. In one suitable embodiment, the bodyside liner 30 is configured to isolate the wearer's skin from liquids held in the absorbent structure 48. In order to present a dryer surface to the wearer, the bodyside liner 30 may be less hydrophilic than the absorbent structure 48 and also sufficiently porous to be readily liquid permeable.

Suitable materials for the bodyside liner 30 are well known in the art and include, for example, porous foams, reticulated foams, apertured plastic films, natural fibers (i.e., wool or cotton fibers), synthetic fibers (i.e., polyester, polypropylene, polyethylene, etc.), or a combination of natural and synthetic fibers. For example, the bodyside liner 30 may comprise meltblown or spunbonded web of polyolefin fibers or a bonded-carded web composed of natural and/or synthetic fibers. The bodyside liner 30 may be composed of substantially hydrophobic material treated with a surfactant or otherwise processed to impart the desired level of wettability and permeability. As an example, surfactant can be applied, in an amount to impart the desired degree of hydrophilicity, by conventional means, such as spraying, printing, brush coating or the like. In one suitable embodiment, the bodyside liner 30 may comprise a nonwoven web of polypropylene spunbond fibers or polyethylene/propylene multicomponent spunbond fibers treated with a surfactant, e.g., octylphenoxypolyethoxyethanol, which is commercially available from Union Carbide of Danbury, Conn. under the trademark TRITON X-102 or equivalent.

Figure 5:
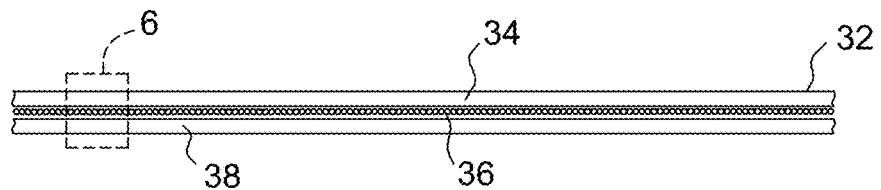
FIG. 5 is an end view of one suitable embodiment of an outer cover of the diaper.
Figure 6:
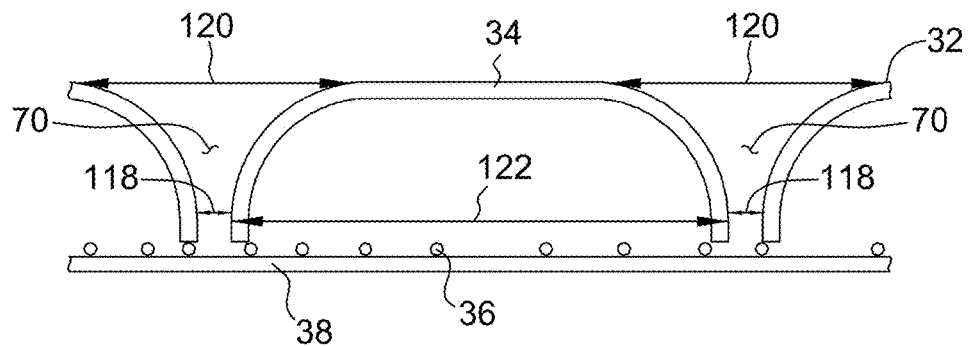
FIG. 6 is an enlarged end view taken from FIG. 5.

The outer cover 32 of the diaper 10, which is illustrated in FIG. 2, defines a garment facing surface of the diaper that is intended to be worn adjacent the clothing of the wearer. In one suitable embodiment, the outer cover 32 is a laminate comprising at least two layers (e.g., a first layer bonded to a second layer). In the illustrated embodiment and as seen in FIGS. 5 and 6, for example, the outer cover 32 comprises a fibrous nonwoven component 34 adhesively bonded (e.g., by adhesive layer 36) to a film 38. In one suitable embodiment, for example, the outer cover 32 may comprise a polypropylene spunbond fabric adhesively bonded using a fiberized adhesive to a stretch-thinned polypropylene film.

In one suitable embodiment, the film 38 is a "breathable" material that permits vapors to escape from the diaper 10 and that is liquid impermeable. Thus, in one embodiment, the film 38 can be configured to retain liquid while allowing vapor to pass. In one suitable configuration, the film 38 can be a micro-porous material that is "breathable" for allowing vapors to escape from the diaper 10 while preventing liquid exudates from passing through. For example, the outer cover 32 may comprise a microporous polymer film or a nonwoven fabric that has been coated or otherwise treated to impart a desired level of liquid impermeability.

It is understood that the breathability of the film 38 can vary greatly without departing from some aspects of this disclosure. In one suitable embodiment, for example, the film 38 has a water vapor transmission rate (WVTR) between about 1,500 grams/$m^2$-24 hours and about 10,000 grams/$m^2$-24 hours as determined by the WVTR test procedure described below. In one particularly suitable embodiment, for example, the film layer has a breathability between about 2,500 grams/$m^2$-24 hours and about 7,000 grams/$m^2$-24 hours as determined by the WVTR test procedure. In another particularly suitable embodiment, for example, the film layer has a breathability between about 3,500 grams/$m^2$-24 hours and about 5,000 grams/$m^2$-24 hours as determined by the WVTR test procedure. In one preferred embodiment, the film 38 has a breathability of about 4,000 grams/$m^2$-24 hours as determined by the WVTR test procedure.

Suitable materials for the film 38 include, but are not limited to, polyolefin films and any other suitable polymeric film that is liquid impermeable and vapor permeable. A suitable micro-porous film is, for example, a PMP-1 film material commercially available from Mitsui Toatsu Chemicals, Inc., Tokyo, Japan, or an XKO-8044 polyolefin film commercially available from 3M Company, Minneapolis, Minn. One suitable liquid impermeable film for use as the film 38 is, for example, a 0.2 millimeter polyethylene film commercially available from Huntsman Packaging of Newport News, Va., U.S.A.

Another material suitable for the film 38 includes a polymer matrix component and a filler component. The polymer matrix preferably includes a polyolefin, and constitutes about 30-90% by weight of the film layer. The film layer also includes a filler component. The filler component may be an organic or inorganic filler, and constitutes about 10-70% by weight of the film layer. The filler(s) and polymer matrix component are initially melt blended, and the blend is extruded into a precursor film layer. The precursor film layer may be extruded as a single-layer film, or may constitute one or more layers in a multilayer film structure. The film is then preferably stretched at an elevated temperature below the melting temperature of the polymer component. As the film is stretched, voids form around the filler particles to form a microporous, breathable film.

The fibrous nonwoven component 34 of the outer cover 32 can comprise any suitable nonwoven including a single layer nonwoven or nonwoven laminate. For example, the nonwoven component 34 consisting of a single layer may be a spunbond web. In one suitable embodiment of the nonwoven component 34 consisting of a nonwoven laminate, the nonwoven component may contain a meltblown layer positioned between two spunbond layers to form a spunbond/meltblown/spunbond ("SMS") laminate. Of course, the nonwoven laminate may have other configuration and possess any desired number of meltblown and spunbond layers, such as spunbond/meltblown/meltblown/spunbond laminates ("SMMS"), spunbond/meltblown laminates ("SM"), etc. In addition to spunbond webs, a variety of other nonwoven webs may also be used to form the nonwoven component 34, such as meltblown webs, bonded carded webs, wet-laid webs, airlaid webs, coform webs, hydraulically entangled webs, etc.

It is understood that the basis weight of the nonwoven component 34 may be any suitable basis weight. In some suitable embodiments, the basis weight of the nonwoven component 34 is between about 8 grams per square meter (gsm) and about 30 gsm and, more specifically, between about 10 gsm and about 18 gsm. For example, suitable basis weights for the nonwoven component 34 include 12 gsm and 15 gsm.

Figure 3:
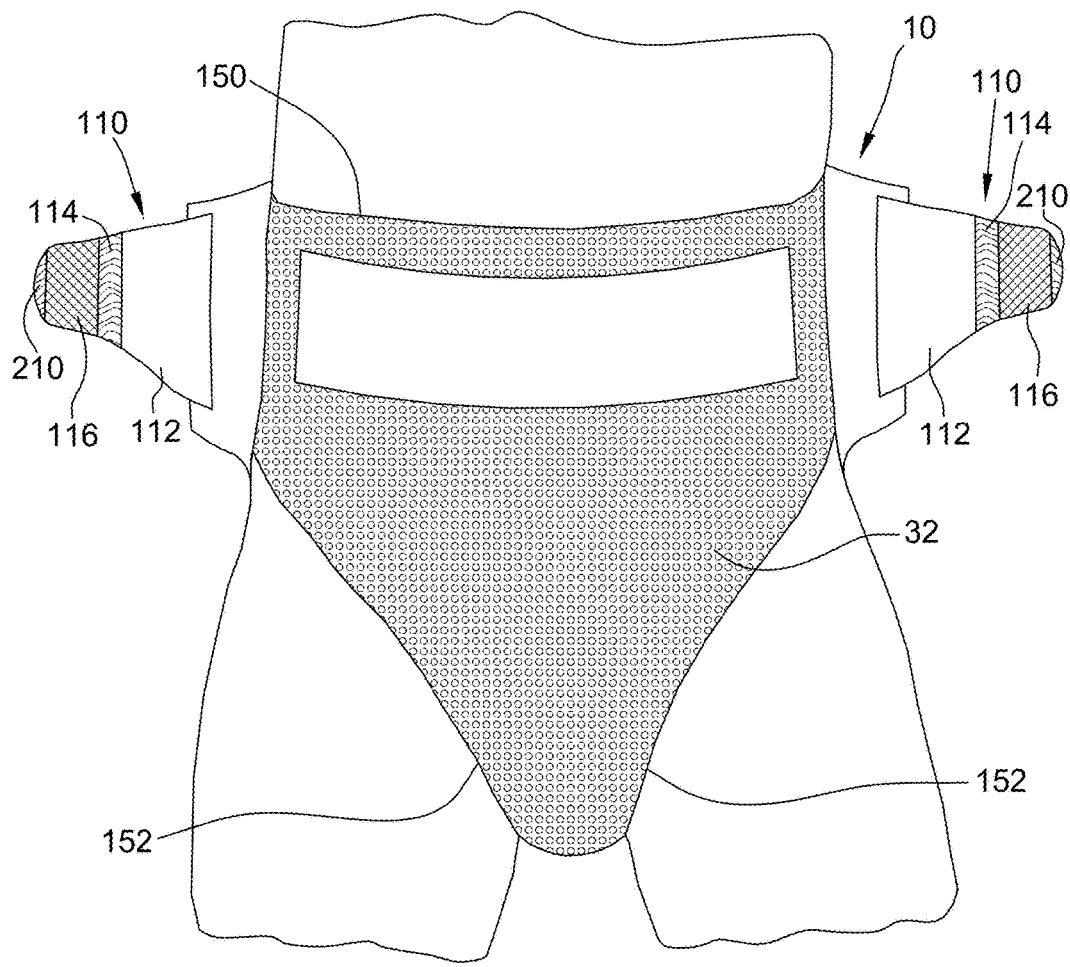
FIG. 3 is a front view of the diaper in a wear configuration with a fastening system being in an unfastened position.

As seen in FIGS. 2 and 3, the nonwoven component 34 of the outer cover has a plurality of apertures 70. In one suitable embodiment and as seen in FIGS. 2 and 3, which are plan views, each of the apertures 70 is generally circular but it is understood that the apertures can have any suitable shape (e.g., elliptical, square, triangular). In one suitable embodiment, the apertures 70 are generally circular (when viewed from above or below—in plan view) and have a diameter (i.e., a first width 118, which can be seen in FIG. 6) between about 0.5 mm and about 4 mm.

As seen in FIG. 6, which is an enlarged end view of the outer cover 32, each of the apertures 70 are generally conical in cross-section. As a result, the apertures 70 have a first width 118 (or "a minimum width") located adjacent the film 38 and a second width 120 (or "a maximum width") located adjacent an outer extend of the nonwoven component 34. In the illustrated embodiment, the first width 118 is substantially less than the second width 120. The illustrated apertures 70, for example, have a first width (or diameter) 118 of approximately 1 mm and a second width (or diameter) 120 of approximately 1.5 mm. In the illustrated embodiment, each of the apertures 70 has generally the same size and shape (i.e., circular apertures having approximately a 1 mm diameter when viewed from the top plan and generally conical when viewed from the end or in cross-section).

Figure 7:
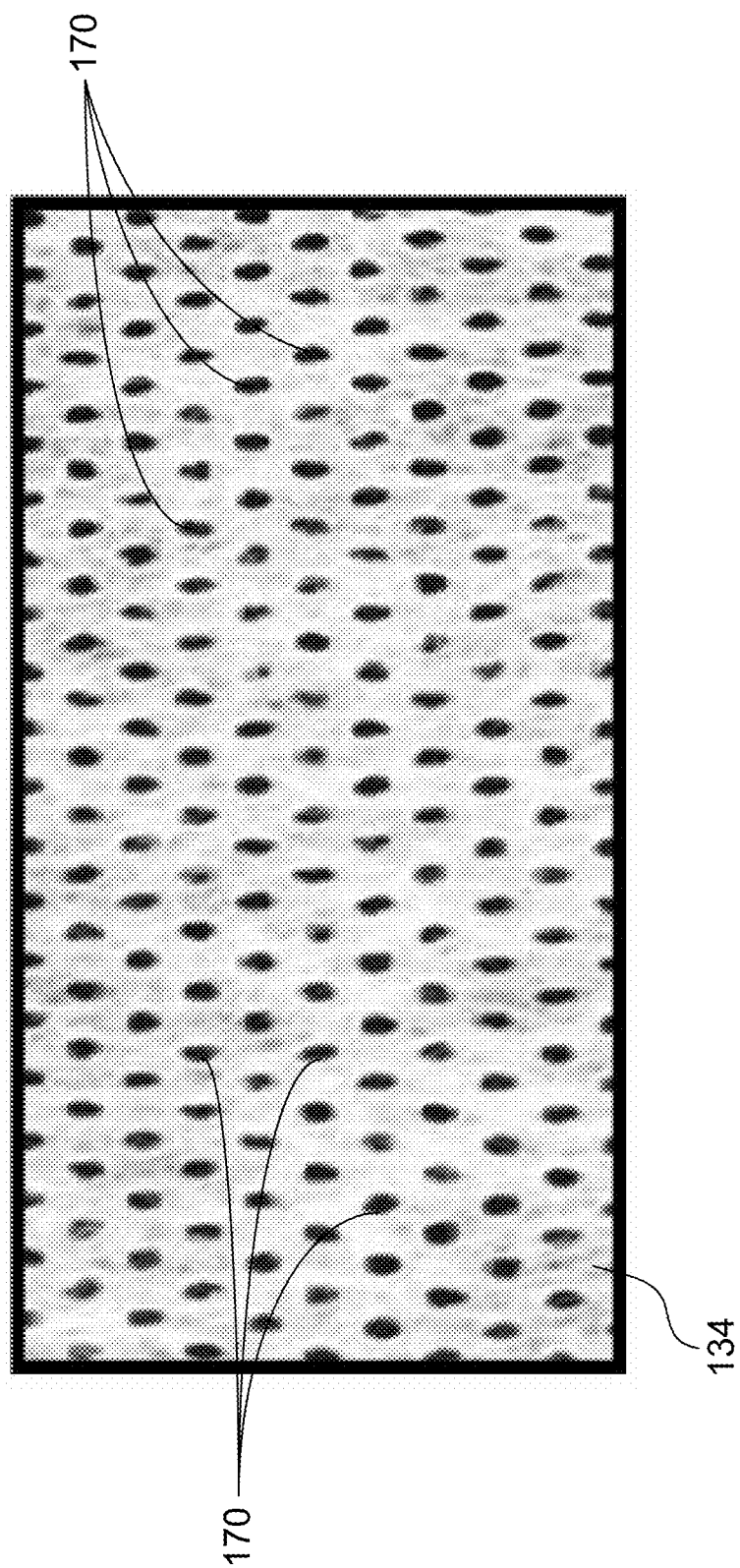
FIG. 7 is a top plan of another suitable embodiment of an outer cover of the diaper.

It is understood that the apertures 70 can have any suitable size and/or shape without departing from some aspects of this disclosure. For example, FIG. 7 illustrates a suitable nonwoven component 134 having generally elliptical apertures 170 when viewed from the top plan. It is contemplated that in some suitable embodiments, the second width 120 can be defined by a width of a channel. For example, the channel can extent between two or more apertures 70 and the apertures can be formed in the bottom of the channel.

It is understood that the nonwoven component 34 of the outer cover 32 can have apertures 70 with different sizes and/or shapes. For example, different parts of the diaper 10 can have different sized and/or shaped apertures 70. In one suitable example, the back and front portions 12, 14 of the diaper 10 may have apertures 70 with larger diameters than the apertures in the crotch portion 16. It is contemplated that in such an embodiment, the crotch portion 16 of the diaper 10 may be free of apertures 70. In another suitable example, the parts of the nonwoven component 34 spaced from the absorbent structure 48 may have apertures 70 with larger diameters than the part corresponding to (e.g., overlying) the absorbent structure 48. It is contemplated that in such an embodiment, the part of the nonwoven component 34 overlying the absorbent structure 48 may be free of apertures 70.

As best seen in FIG. 2, the apertures 70 define a plurality of columns that extend in the longitudinal direction 42 of the diaper and a plurality of rows that extend in the transverse direction 44 of the diaper. In one suitable embodiment, each of the apertures 70 is spaced approximately equally from the adjacent apertures. In other words, each of the columns and each of the rows are spaced apart by approximately the same distance. In one suitable embodiment, each of the apertures is spaced apart from the adjacent apertures (as measured from an edge of one aperture to the closest edge of an adjacent aperture) by a distance 122 (FIG. 6) between about 0.5 mm and about 6 mm. In the illustrated embodiment, for example, the distance 122 between adjacent apertures 70 is approximately 1 mm. It is understood that the spacing between apertures 70 can be any suitable distance and vary between apertures. Thus, the apertures 70 can have any suitable spacing including random. Moreover, the density of the apertures 70 in the nonwoven component 34 can range from approximately 9 per square centimeter to approximately 36 per square centimeter. In the illustrated embodiment, for example, the density of the apertures 70 is approximately 18 apertures by square centimeter.

It is understood that the apertures 70 in the nonwoven component 34 can have any suitable spacing and density. It is also understood that the spacing and/or density of the apertures 70 can vary in different parts of the nonwoven component 34. Thus, different parts of the nonwoven component 34 can have more or fewer apertures 70 than other parts without departing from some aspects of this disclosure.

As seen in FIG. 6, which is an enlarged end view of the outer cover 32 taken from FIG. 5, the nonwoven component 34 generally defines a plurality of domed areas, which appear generally as arches in FIG. 6, that extend between the apertures 70. As illustrated therein, the nonwoven component 34 is adhesively bonded to the film 38 by the adhesive 36 at locations adjacent the open ends of the projections which form the apertures 70. The portions of the nonwoven component 34 remote from the apertures (e.g., the domed areas) are spaced from the film 38 due to the air gap that is created by the fibers of the nonwoven material being displaced orthogonally from the X-Y plane of the nonwoven component when the apertures 70 are formed therein. The cone-like projections so formed by the aperturing process facilitate what is believed to be the increased air handling capability of the resultant laminate which forms the outer cover 32 and thus the ability of the laminate to provide improved capacity to reduce the wet or damp feel normally associated with the breathable outer cover composites of personal care absorbent articles such as, for example, diapers. Spacing a significant portion of the nonwoven component 34 from the film 38, as illustrated in FIG. 6, also creates loft in the nonwoven component. The loft adds bulk and resiliency to the nonwoven component 34 which contributes to the overall increased comfort and feel of the outer cover 32 described herein. Thus, the nonwoven component 34 having apertures 70 as disclosed herein has greater bulk and resiliency than the same nonwoven component without apertures.

Moreover, spacing portions of the nonwoven component 34 from the film 38 inhibits the outer cover from feeling wet or damp to the user. As mentioned above, sometimes during the use of absorbent articles relatively warm vapor passes through the outer cover, cools, and condenses on the outer cover and more specifically on the film. Thus, any condensation that collects on the film 38 of the outer cover 32 disclosed herein will be spaced from the user by the nonwoven component 34. As a result, the outer cover 32 disclosed herein will likely not feel wet or damp to the user. It is understood that a similar result could be achieved by having a nonwoven component with a greater basis weight. Doing so, however, would significantly increase the costs of the outer cover.

Furthermore, in one suitable embodiment of the present disclosure, the apertures 70 in the nonwoven component 34 are readily visible to the user. Thus, the apertures 70 can provide a visual cue to the user that the diaper 10 includes a breathable outer cover and, more specifically, that the film 38 is breathable.

As mentioned above, the film 38 and the nonwoven component 34 of the outer cover 32 are suitably adhesively bonded to one another. It is understood, however, that in some embodiments the nonwoven component 34 and film 38 can be bonded together using any suitable bonding technique. For example, in some suitable embodiments, the nonwoven component 34 can be thermo-bonded or pressure bonded to the film 38.

In one suitable embodiment, the film 38 and the nonwoven component 34 have approximately the same length and the same width and are aligned with one another (i.e., the film 38 and the nonwoven component 34 are coextensive). In another suitable embodiment, as seen in FIGS. 1 and 2, the width of the film 38 is significantly less than the width of the nonwoven component 34. Thus, the longitudinally extending side edges of the film 38 are spaced considerably inward from the side edges 24 of the diaper 10, which are defined at least in part by the nonwoven component 34. In the illustrated embodiment, the width of the film 38 is approximately equal to or slightly larger than the width of the absorbent structure 48. As a result, the absorbent structure 48, which is intended to absorb and retain liquid insults, is sufficiently covered by the film 38. It is understood that the film 38 can have any suitable size and shape without departing from some aspects of this disclosure.

Figure 12:
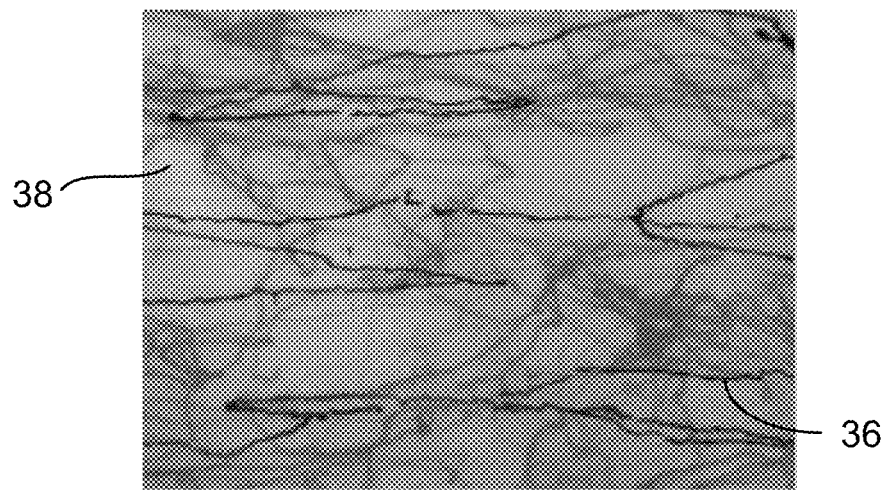
FIG. 12 is a photograph showing fiberized adhesive disposed on the film of the apertured SMS laminated sample.

As seen in FIGS. 5 and 6, the film 38 and nonwoven component 34 are bonded together in a face-to-face relationship. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. Examples of suitable adhesives include elastomeric adhesives (i.e. materials capable of at least 75% elongation without rupture), such as aqueous-based styrene butadiene adhesives, neoprene, polyvinyl chloride, vinyl copolymers, polyamides, and ethylene vinyl terpolymers. In one suitable embodiment and is seen in FIG. 12, the adhesive 36 is a fiberized adhesive. Suitably, the adhesive is applied to the film 38 in an amount between about 0.5 gsm and about 2 gsm prior to the nonwoven component 34 being laminated to the film. In the illustrated embodiment, for example, approximately 0.9 gsm of adhesive is applied to the film. It is understood that in other suitable embodiments, the adhesive can be applied to the nonwoven component 34 before being laminated to the film 38. It is further understood that any suitable amount of adhesive can be used.

Figure 8:
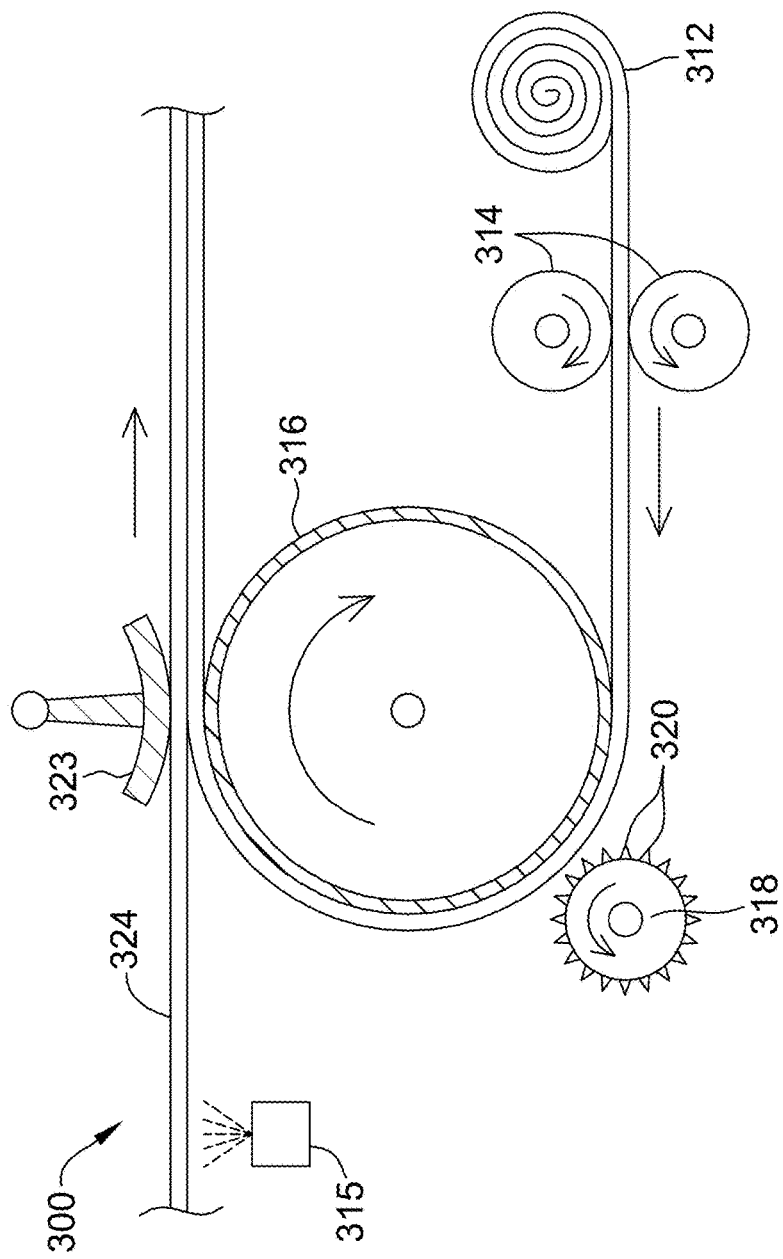
FIG. 8 is a schematic illustrating one suitable method of making the outer cover.

In one suitable embodiment, the apertures 70 in the nonwoven component 34 are suitably formed by needling. Needling is process wherein a plurality of needles (or pins) is driven into or through the nonwoven. With reference to FIG. 8, which illustrates one suitable embodiment of apparatus, indicated generally at 300, for making the outer cover 32, an incoming continuous web 312 of suitable nonwoven material may be fed to an anvil roll 316 via a web feeding assembly such as, e.g., one or more drive rollers 314. In the illustrated embodiment, the anvil roll 316 is a vacuum roll but it is contemplated that other suitable web handling devices can be used. The anvil roll 316 may internally contain or otherwise be connected to a suitable vacuum source (such as, e.g., a vacuum pump, a vacuum chamber, etc., not shown) which is capable of selectively applying a vacuum pressure (i.e., negative pressure) through one or more vacuum holes such that materials provided to the outer surface of the anvil roll are generally drawn to and secured against the outer surface.

The apparatus 300 illustrated in FIG. 8 further comprises a needling roll 318 (broadly, "a needling station") comprising a plurality of needles 320. In one suitable embodiment, each of the needles 320 is generally conical in shape. It is understood, however, that the needles can have any suitable size or shape without departing from some aspects of this disclosure. The needles 320 are configured to penetrate the nonwoven web 312 a predetermined depth as the nonwoven web is carried by the anvil roll 316 past the needling roll 318. It is understood that in other suitable methods (e.g., air or water jets) of deflecting fibers of the nonwoven web 312 in the z-direction (out of the x and y plane) and aperturing the nonwoven web 312 can be used without departing from some aspects of this disclosure.

As seen in FIG. 8, a continuously moving web 324 of suitable film 38 material is delivered to the anvil roll 316. In the illustrated embodiment, a suitable adhesive, such as a fiberized adhesive, is applied to the web 324 at an adhesive station 315 prior to or upon reaching the anvil roll 316. More specifically, the web 324 of film material having adhesive thereon and the nonwoven web 312 are directed through a nip defined by the anvil roll 316 and a stomper 323 (or other suitable device, e.g., a roll). It is understood that the stomper 323 can be omitted. In such an embodiment, the nonwoven web 312 is adhered to the web 324 of film material without the use of a nip. It is contemplated that the outer cover 32 can be made using any suitable method without departing from some aspects of this disclosure.

With reference again to FIGS. 1 and 2, the bodyside liner 30 and the outer cover 32 are disposed on opposite sides of the absorbent structure 48. Thus, the absorbent structure 48 is disposed between the bodyside liner 30 and the outer cover 32. In one suitable embodiment, the bodyside liner 30 and the outer cover 32 are joined to each other around the outer periphery of the absorbent structure 48 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

In one suitable embodiment, the bodyside liner 30 and outer cover 32 (and more specifically the nonwoven component 34) are generally coextensive. That is, the bodyside liner 30 and the outer cover 32 have generally the same size and shape and are positioned such that the periphery of the bodyside liner is generally aligned with the periphery of the outer cover 32. In the illustrated embodiment, the bodyside liner 30 and outer cover 32 are generally in face-to-face relationship and bonded together beyond the extent of the film 38. It is understood, however, that the bodyside liner 30 and outer cover 32 can have any suitable size and shape including embodiments wherein the bodyside liner 30 has a size and shape that differs from the size and shape of the outer cover 32.

As mentioned above, the absorbent structure 48 is positioned between the bodyside liner 30 and the outer cover 32. The absorbent structure 48 is generally conformable and capable of absorbing and retaining liquid body exudates. The absorbent structure 48 can include superabsorbent material, staple fibers, binder fibers, and the like, and combinations thereof as is known in the art. The absorbent structure 48 may have any of a number of shapes and sizes. For example, the composite absorbent core may be rectangular, I-shaped or T-shaped. The size and absorbent capacity of the absorbent structure 48 should be compatible with the size of the intended wearer and the fluid loading imparted by the intended use of the diaper 10.

In one suitable embodiment, the diaper 10 may include a surge portion (not shown) disposed between the absorbent structure 48 and the bodyside liner 30. The surge portion serves to quickly collect and temporarily hold liquids discharged by the wearer and then release the liquids to the absorbent structure 48. Various woven and nonwoven materials can be used to construct the surge portion. For example, the surge portion may be a layer of a spunbonded or meltblown web of polyolefin fibers. The surge portion may also be a bonded carded web of natural and synthetic fibers. The surge portion may be a substantially hydrophobic material and, optionally, can be treated with a surfactant or otherwise to impart a desired level of wettability and hydrophilicity.

In the illustrated embodiment, the absorbent structure 48 includes a tissue wrapsheet 90. The tissue wrapsheet 90 helps to maintain the integrity of some absorbent structures, such as airlaid fibrous structures. In addition, the tissue wrapsheet 90 helps to distribute liquid over the absorbent structure 48, particularly when using a material with excellent wicking properties such as absorbent cellulosic materials. Examples of common tissue wrapsheet materials include creped wadding or a high wet-strength tissue. In addition, hydrophilic nonwoven fabrics may also be used as an absorbent core wrapsheet; see commonly assigned U.S. Pat. No. 5,458,592 to Abuto et al., the entire contents of which are incorporated herein by reference.

With reference to FIGS. 1 and 2, the diaper 10 includes a pair of elasticized, longitudinally-extending leg cuffs 74. The leg cuffs 74 are adapted to fit about the legs of a wearer in use and serve as a mechanical barrier to the lateral flow of body exudates. In one suitable embodiment, the leg cuffs 74 can be formed by portions of the outer cover 32, and/or bodyside liner 30, which extend beyond the longitudinal sides of the absorbent structure 48. In another suitable embodiment and illustrated in FIGS. 1 and 2, the leg cuffs 74 can be formed from separate materials (e.g., stands of leg elastics) joined to the outer cover 32 and/or other components of the diaper 10.

The diaper 10 may further include a front waist elastic (not shown) and/or a back waist elastic 72. In the illustrated embodiment, for example, the diaper 10 has a back waist elastic 72 but not a front waist elastic. The back waist elastic 72 is arranged to draw and hold the diaper 10 against the wearer, particularly against the waist of the wearer.

Materials suitable for use in forming leg cuffs 74 and/or waist elastics 72 are known to those skilled in the art. Examples of such materials are strands or ribbons of a polymeric, elastomeric material which are adhered to the diaper 10 in a stretched position, or which are attached to the diaper while the diaper is pleated, such that elastic constrictive forces are imparted to the diaper 10. The leg cuffs 74 and/or waist elastics 72 may have any configuration which provides the desired performance. The leg cuffs 74 may be generally straight or optionally curved (as illustrated in FIGS. 1 and 3) to more closely fit the contours of the legs of the wearer. As used herein, "elastic", "elastomeric", and the like refer to the ability of a material or composite to be elongated by at least about 50 percent and upon relaxation to return to within at least 50 percent of its original length.

The leg cuffs 74 and/or waist elastics 72 may be attached to the diaper 10 in any way known to those skilled in the art. For example, the cuffs 74 and/or elastics 72 may be joined to the diaper 10 by ultrasonic bonding, thermal bonding, adhesive bonding, and the like, and combinations thereof.

The diaper 10 may also include a pair of containment flaps (not shown) that extend longitudinally along the diaper 10 and are adapted to provide a barrier to the lateral flow of body exudates as is known in the art. The containment flaps can be connected to the bodyside liner or other components of the diaper 10. Suitable configurations of the containment flaps are described, for example, in U.S. Pat. No. 5,599,338 issued Feb. 4, 1997, to K. Enloe, the entirety of which is incorporated herein by reference.

As seen in FIGS. 1 and 2, the back portion 14 of the diaper includes a pair of back ears, indicated generally at 110. In one suitable embodiment, the back ears 110 can be formed from extensions of the bodyside liner 30, the outer cover 32, or the combinations of both the bodyside liner and the outer cover. In another suitable embodiment and as illustrated in FIGS. 1 and 2, the back ears 110 can be formed as separate components and attached to the bodyside liner 30, the outer cover 32, and/or both the bodyside liner and the outer cover as is known in the art. In the illustrated embodiment, the back ears 110 are attached to the body-facing surface of the bodyside liner 30 such that the attached portion of the ears are disposed between the wearer's body and bodyside liner when the diaper is worn.

In one suitable embodiment, each of the back ears 110 includes an elastomeric portion 112, a non-elastomeric portion 114, and a fastening component 116 mounted to the non-elastomeric portion (FIG. 1). The elastomeric portions 112 of the back ears 110 can be formed from any type of elastomeric material capable of performing as described herein. In one suitable embodiment, the elastomeric material will be stretchable in at least one direction (e.g., in the lateral direction 44 of the diaper 10 as viewed in FIG. 1) and preferably, the elastomeric material will be stretchable in two directions (e.g., in both the longitudinal direction 42 and the lateral direction 44 of the diaper as viewed in FIG. 1). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 112 of the back ears 110 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 112 of the back ears 110 can be formed from a stretch-bonded-laminate (SBL) material, a neck-bonded-laminate (NBL) material, an elastomeric film, an elastomeric foam material, or the like.

With reference still to FIG. 1, each of the non-elastomeric portions 114 of the back ears 110 is attached to a respective one of the elastomeric portions 112 and the first fastening components 116 (such as a hook material) are in turn disposed on the non-elastomeric portions. As illustrated in FIGS. 1 and 2, the non-elastomeric portions 114 of the back ears 110 extend in part transversely outward of the respective elastomeric portion 112 and the first fastening components 116 of each of the non-elastomeric portions 114 are configured for engaging a loop component disposed in the front portion 12 of the diaper 10 in the wear configuration, as described in more detail below.

As seen best in FIG. 1, each of the illustrated non-elastomeric portions 114 further comprise a grip region 210 transversely outward of the first fastening component 116 for use in manually gripping and manipulating the non-elastomeric portion and more broadly the respective back ear 110 relative to the diaper 10. The grip region 210 is non-attachable to the diaper 10. The term "non-attachable" as used in this instance means that the grip region 210 is not releasably or otherwise removably attachable to the diaper 10, nor is the grip region permanently attached to the diaper. In one embodiment, the grip region 210 extends transversely outward from the respective first fastener component 116 a distance of at least about 1 mm, such as in the range of about 1 mm to about 10 mm to provide sufficient unattached material for readily gripping and pulling on the non-elastomeric portion 114.

Figure 4:
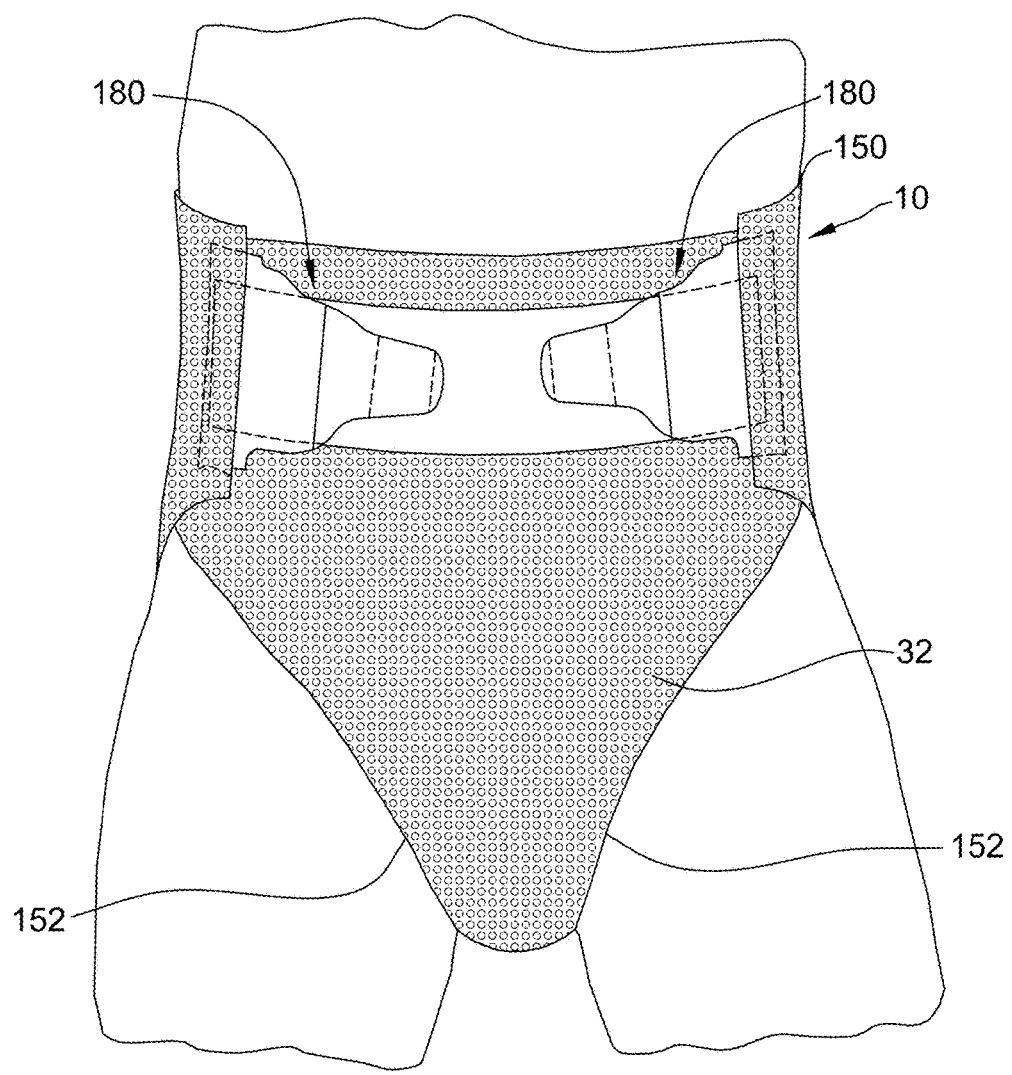
FIG. 4 is a front view of the diaper in the wear configuration with the fastening system being fastened.

As illustrated in FIGS. 3 and 4, the diaper 10 can be selectively moved to a fastened or wear configuration by attaching the back portion 14 (and more specifically the back ears 110) to the front portion 12 using a fastening system, indicated generally at 180, to define a three-dimensional wear configuration of the diaper, having a waist opening 150 and a pair of leg openings 152. Although the diaper 10 illustrated in FIGS. 3 and 4 shows the back portion 14 (and more specifically the back ears 110) overlapping the front portion 12 upon connection thereto, which is convenient, the diaper can also be configured so that the front portion overlaps the back portion when connected.

EXPERIMENTS

Four outer cover samples were tested for water vapor transmission rate (WVTR), gapping distance between nonwoven and film, equivalent-circular diameter (ECD), percent open area, spacing between open areas, peel strength, and adhesive analysis as described below. The four outer cover samples tested consisted of two control samples and two samples made in accordance with the present disclosure.

The two control samples were 1) a spunbond/meltblown/spunbond ("SMS") web having a basis weight of about 12 gsm adhesively bonded to a polymeric film; and 2) a spunbond web having a basis weight of about 15 gsm adhesively bonded to a polymeric film.

The two samples made in accordance with the present disclosure were 1) an apertured spunbond/meltblown/spunbond ("SMS") web having a basis weight of about 12 gsm adhesively bonded to a polymeric film; and 2) an apertured spunbond ("SB") web having a basis weight of about 15 gsm adhesively bonded to a polymeric film.

Each of the samples was made using the same materials and processes except that the two samples made in accordance with the present disclosure were needled prior to being adhesively bonded to the polymeric film. More specifically, the film for each of the samples was a 17 gsm breathable polyethylene film with a WVTR of 4000 grams/m$^2$-24 hours available from Hans Chemical Co., Ltd. of Daegu, Korea. The SMS material was a 12 gsm polypropylene spunbond-meltblown-spunbond available from TORAY Advanced Materials Korea Inc. of Kyungbuk Province, Korea. The SB material was a 15 gsm spunbond available from Yuhan-Kimberly Taejon Mill of TaeJon City, Korea under the name T-Soft. The aperture SB and SMS samples were apertured by Korea Vilene Co., Ltd. of Kyunggi-do, Korea using a needle punch having 18 pins/cm$^2$ to form apertures having approximately 1 mm diameters.

Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), Water Vapor Transmission Rate Mocon/EDANA, Part 1 METHOD NUMBER WSP 70.5 which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm, airgap}$$

Calculations:

WVTR: The calculation of the WVTR uses the formula:

$$WVTR = F\rho_{sat}(T)RH/Ap_{sat}(T)(1-RH))$$

where:

F=The flow of water vapor in cc/min., $\rho_{sat}(T)$=The density of water in saturated air at temperature T, RH=The relative humidity at specified locations in the cell, A=The cross sectional area of the cell, and, $p_{sat}$=The saturation vapor pressure of water vapor at temperature T.

TABLE 1

Results of the WVTR Testing
WVTR Testing

|  | Average | StdDev |
|---|---|---|
| Laminate | | |
| 12 gsm non-perfed SMS | 3954 | 219 |
| 12 gsm perfed SMS | 3552 | 114 |
| 15 gsm non-perfed SB | 3580 | 59 |
| 15 gsm perfed SB | 3795 | 304 |
| Film Removed from Laminate | | |
| 12 gsm non-perfed SMS | 4021 | 304 |
| 12 gsm perfed SMS | 4024 | 76 |
| 15 gsm non-perfed SB | 3814 | 188 |
| 15 gsm perfed SB | 3873 | 229 |
| Poly Film Only | | |
| "4000 WVTR" | 3797 | 173 |

The WVTR testing data for the four outer cover samples tested indicated that the apertures in the two samples made in accordance with the present disclosure did not impact the WVTR value. That is, the WVTR data for the two control samples were substantially similar to the corresponding sample made in accordance with the present invention.

Specifically, the control SMS laminate sample had a WVTR average of 3954 grams/m²-24 hours whereas the apertured SMS laminate sample had an WVTR average of 3552 grams/m²-24 hours. Moreover, the film in the control sample with the SMS nonwoven and adhesive removed had an WVTR average of 4021 grams/m²-24 hours whereas the film in the apertured sample with the apertures SMS nonwoven and adhesive removed had an WVTR average of 4024 grams/m²-24 hours.

The control SB laminate sample had an WVTR average of 3580 grams/m²-24 hours whereas the apertured SB laminate sample had an WVTR average of 3795 grams/m²-24 hours. Moreover, the film in the control sample with the SB nonwoven and adhesive removed had an WVTR average of 3814 grams/m²-24 hours whereas the film in the apertured sample with the apertured SB nonwoven and adhesive removed had an WVTR average of 3873 grams/m²-24 hours.

The film, which was the same for all four samples, had a WVTR average of 3797 grams/m²-24 hours.

In one particularly suitable embodiment, the outer cover 32 disclosed herein has a breathability between about 1,500 grams/m²-24 hours and about 10,000 grams/m²-24 hours as determined by the WVTR test procedure. In one preferred embodiment, the outer cover has a breathability between about 2,500 grams/m²-24 and about 7,000 grams/m²-24 hours as determined by the WVTR test procedure. In another preferred embodiment, the outer cover has a breathability between about 3,500 grams/m²-24 and about 5,000 grams/m²-24 hours as determined by the WVTR test procedure. In a preferably suited embodiment, the outer cover has a breathability of about 4,000 grams/m²-24 hours as determined by the WVTR test procedure.

Gapping Distance Between Nonwoven and Film

The gapping distance between the laminated nonwoven and film in the outer cover (OC) samples was determined using the image analysis measurement method described herein (broadly, the "gapping distance procedure"). The image analysis method determined a dimensional numeric distance value between the outer cover's two most outer layers using a specific image analysis measurement of the separation or gapping between the layers. The layer gapping method was performed using conventional optical image analysis techniques to detect cross-sectional layer regions of both outermost nonwoven and adjacent film layer components and then measure a mean linear distance value between the two when viewed using a camera with incident low-angle illumination. The resulting measurement data were used to compare the gapping distance characteristics of different types of outer cover layer configurations.

Prior to performing image analysis measurements, the sample of interest was prepared in such a way to allow visualization of a representative cross-section that includes all outer cover component layers. Outer cover sample pieces were cut from a diaper product using a scissors into four pieces of approximately 1 inch by 1 inch in size. Ideally each piece should be cut from a separate, individual diaper product. Cross-sectioning of the pieces was performed in parallel to the machine direction along a straight edge (e.g. ruler) that also anchors a representative sample piece down during sectioning. Cross-sectioning was performed along the straight edge in the machine direction and thru the outer cover sample piece using a new, previously unused single edge carbon steel blue blade (PAL). Such blades for cross-sectioning can be acquired from Electron Microscopy Sciences of Hatfield, Pa. (Cat. #71974). A fresh, previously unused blade was used for each new cross-sectional cut. The cross-sectioned face was then mounted so that it could be viewed using a video camera mounted on a stereo microscope. The mount itself and any background behind the sample that would be viewed by the camera was darkened using non-reflective black tape and black construction paper, respectively. Four separate cross-sections were cut and mounted separately from which approximately two layering gapping values were determined from each. The inner most layer of the outer cover was in contact with the sample mount, so that the layer gap to be measured was away from the sample mount surface. An adherent such as transparent, double-sided tape was used to gently attach the sample piece to the mount.

A Leica Microsystems M205 stereo microscope system was used to acquire cross-sectional images of outer cover layers and any gapping between them. The system was controlled with Leica Application Suite software (version 4.3.0). The stereo microscope was set to a magnification of 25.0×. The digital camera was a Leica Microsystems model DFC 450C which was set to an exposure time of 80 milli-seconds, a gamma setting of 1.0, and was operated in monochromatic mode. Illumination of the mounted cross-section was performed using the LED MCI mode where the top two of three lights in each of the three LED units were powered on. The two outside LED units were placed at the outer most positions possible. Prior to imaging the samples, the optics where shading corrected using the tool provided in the Leica Application Suite software. A blank, white, slightly out of focus background was used for creating the shading correction image.

The darkened sample mount exposing the cross-sectioned sample layers was placed under the optical axis of the stereo microscope. The sample mount was oriented so the sample cross-section runs in the horizontal direction of the resulting image with the two outermost layers of interest at the bottom of the horizontal-running cross-section as shown in the image. The cross-sectional face was illuminated with the LED MCI modality of lighting as previously described. The illumination level of the LED lights was controlled with Leica Application Suite software and was adjusted so that the image gray-level histogram was positioned approximately in the middle of the range displayed and did not possess any over exposed regions. After the focus was properly adjusted to optimize the clarity of the cross-sectional edge of the layers, an image was acquired. The image was then saved using a unique image prefix name corresponding to each sample code followed by the replicate number of the image acquired (i.e. 1-8). Two images were acquired and saved per cross-sectional piece.

The image analysis software platform used to perform measurements was a QWIN Pro (Version 3.5.1) available from Leica Microsystems, having an office in Heerbrugg, Switzerland. The system and images were calibrated using the values obtained from the Leica Application Suite stereo microscope system. Units of microns per pixel were used for the calibration in the QWIN Pro software.

An image analysis algorithm was used to process images as well as perform measurements using Quantimet User Interactive Programming System (QUIPS) language. The image analysis algorithm is reproduced below.

```
NAME = Z – Distance Between Layers – 1
PURPOSE = Measures distance between adjacent layers
(gaps) in multi-layer structure
CONDITIONS = X-sectional images acquired on Leica
M205 stereo (25.0X mag); DFC 450C camera (80 msec);
LED MCI illum. (max spread, top two on)
DATE = September 17, 2013
DEFINE VARIABLES & OPEN FILES
-- Spreadsheet file location for data output
Open File (C:\Data\53152\data.xls, channel #1)
FIELDS = 8
SAMPLE ID AND SET UP
```

-continued

```
Enter Results Header
File Results Header (channel #1)
File Line (channel #1)
Measure frame (x 31, y 61, Width 2498, Height 1858)
Image frame (x 0, y 0, Width 2560, Height 1920)
-- Calibration value = 2.16 um/pixel
CALVALUE = 2.16
Calibration (Local)
-- Binary graphics for vertical measurement bars (10)
Graphics   (Grid, 10 × 0 Lines, Grid Size 2349 × 1641,
Origin 91 × 71, Thickness 5, Orientation 0.000000, to
Binary10 Cleared)
-- Binary graphics to ensure ends of layers are
connected for image processing
Graphics   (Grid, 2 × 0 Lines, Grid Size 2480 × 1735,
Origin 40 × 71, Thickness 10, Orientation 0.000000,
to Binary11 Cleared)
-- Enter image prefix name of images to analyze
PauseText ("Enter image file prefix name.")
Input    (TITLE$)
File    ("Rep. No.", channel #1, field width: 8, left
justified)
File    ("Distance (um)", channel #1, field width: 14,
left justified)
File Line    (channel #1)
REPLICATE SAMPLING LOOP
For (REPLICATE = 1 to FIELDS, step 1)
Clear Feature Histogram #1
Clear Accepts
IMAGE ACQUISITION AND DETECTION
ACQOUTPUT = 0
-- Image file location pathway
ACQFILE$ = "C:\Images\53152 - Faulks\OC Cross-
sections\"+TITLE$+" - "+STR$(REPLICATE)+".tif"
Read image (from file ACQFILE$ into ACQOUTPUT)
-- Detect layer edges
PauseText ("Optimize the threshold so that layers of
interest are detected.")
Detect [PAUSE] (whiter than 60, from Image0 into
Binary0)
IMAGE PROCESSING
PauseText ("Use mouse and edit tools to ensure layers
of interest are selected across entire measure frame
width.")
Binary Edit [PAUSE] (Accept from Binary0 to Binary1,
nib Fill, width 2)
Binary Amend (Close from Binary1 to Binary2, cycles
10, operator Horiz, edge erode on) Binary Amend
(Open from Binary2 to Binary3, cycles 3, operator
Disc, edge erode on)
Binary Logical    (C = A OR B: C Binary3, A Binary3,
B Binary11)
Binary Identify    (FillHoles from Binary3 to Binary4)
Binary Logical    (C = A XOR B: C Binary5, A Binary3,
B Binary4)
Binary Amend    (Close from Binary5 to Binary6, cycles
6, operator Disc, edge erode on)
Binary Logical    (C = A AND B:   C Binary7, A Binary6,
B Binary10)
MEASURE LAYER GAP DISTANCE
Measure feature (plane Binary7, 8 ferets, minimum
area: 12, grey image: Image0 )    Selected
parameters: X FCP, Y FCP, Feret90
TOTLENGTH = Field Sum of (PFERET90(FTR) )
MEANLENGTH = TOTLENGTH/10
OUTPUT DATA - to spreadsheet
File (REPLICATE, channel #1, field width: 8, left
justified, 0 digits after '.')
File (MEANLENGTH, channel #1, field width: 7, left
justified, 1 digit after '.')
File Line (channel #1)
Next (REPLICATE)
Close File (channel #1)
END
```

The QUIPS algorithm was executed using the QWIN Pro software platform. The analyst was initially prompted to enter sample identification information which was sent to a designated EXCEL file to which the measurement data was also subsequently sent.

The analyst was then prompted to enter the image file prefix name used during the image acquisition step previously described.

The algorithm read in the first image and the analyst was prompted to optimize the detection threshold so that the layers of interest were detected. To aid in this optimizing process, the analyst could toggle the 'control' and 'B' keys on the keyboard simultaneously to turn the overlying binary image on and off to assess how closely the adjusted binary matches with the edge boundaries of the sample layers shown in the cross-section.

The analyst was next prompted to use the computer mouse and edit tools in the Binary Edit mode window to ensure the layers of interest were selected across the entire measure frame width. The initial edit mode was set to 'accept' so that the analyst can choose the nonwoven and poly film layers from the already detected binary as best as possible. When selected using the mouse, the selected regions were shown in green on the display screen. If the earlier detection step was optimized well, this was easy and straightforward. If not, the analyst needed to use the 'Draw' function to complete regions of a layer that did not detect fully. When finished, the green binary overlaying the layer edges of interest were continuous from the left to right boundaries of the inner measurement frame. In some cases, there were regions where the two layers come together to form a single layer. If a mistake was made during the editing process, the analyst can simply reset to the original detected binary by clicking on the 'Undo' button located with the Binary Edit window and begin the selection process again until accurate and optimal layer selections were made.

After optimization of layer detection and selection, the algorithm then automatically performed additional image processing steps and then measurements. Data was transferred into the designated EXCEL spreadsheet file. In the EXCEL file, the sample information, image replicate number and gapping distance data was displayed.

The analyst was then again prompted to repeat the detection optimization and layer selections on seven more images until all eight images had been analyzed and the data transmitted to the EXCEL file.

Figure 13:
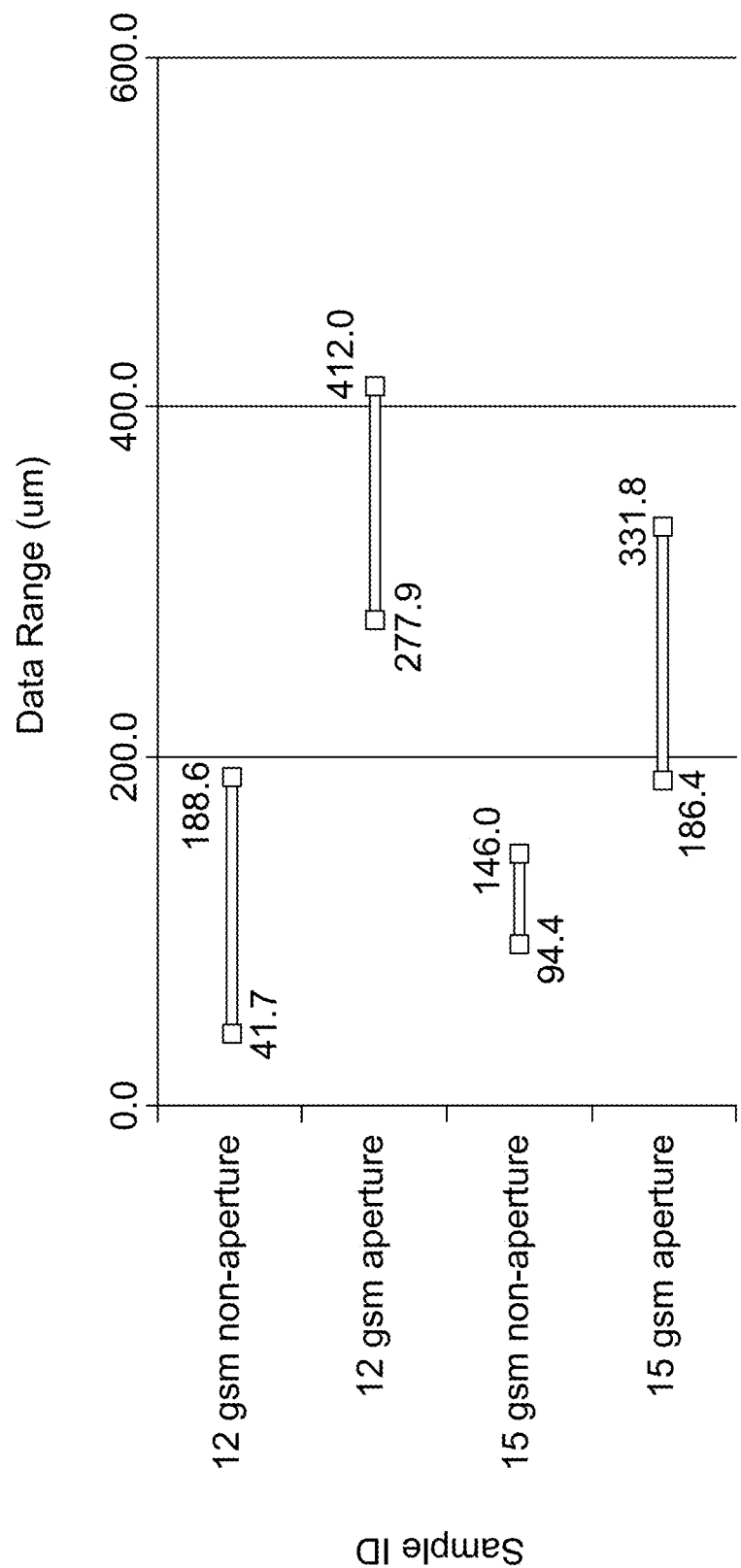
FIG. 13 is a graph illustrating a Student's T Confidence Limit Ranges for testing related to a gapping distance between a laminated nonwoven and a film in an outer cover.

The QUIPS algorithm provided eight replicate layer gapping measurements for a single sample so that eight values were generated per sample. The final sample mean spread value was usually based on an N=8 analyses from eight, separate sub-sample measurements. A comparison between different samples was performed using a Student's T analysis at the 90% confidence level (FIG. 13).

Figure 9:
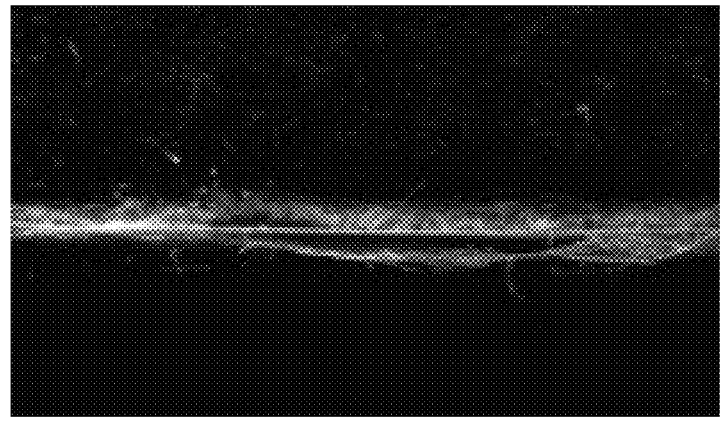
FIG. 9 is a photograph of a cross-section taken from a SMS laminated control sample comprising a SMS nonwoven adhesively laminated to a film.
Figure 10:
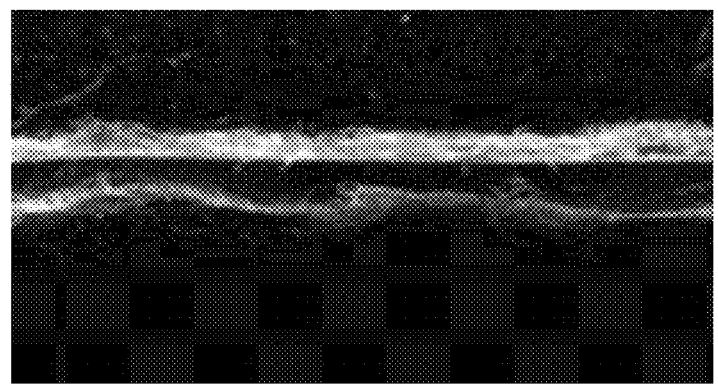
FIG. 10 is a photograph of a cross-section taken from an apertured SMS laminated sample comprising an apertured SMS nonwoven adhesively laminated to a film in accordance with present disclosure.

Cross-sections of each of the four samples were acquired in the MD by razor cutting and optical microscopy. FIG. 9 is a photograph of the cross-section taken from the SMS laminate control sample and FIG. 10 is a photograph of the cross-section taken from the apertured SMS laminated sample.

Analysis of all four cross-sections showed that the apertured samples have a significantly larger gap than the controlled samples. More specifically, the apertured SMS laminate had a mean gap of 345 µm whereas the control SMS laminate had a mean gap of 115 µm. The apertured SB laminate had a mean gap of 259 µm whereas the control SM laminate had a mean gap of 120 µm.

TABLE 2

Gapping Distance between Nonwoven and Film

| Sample ID | Layer Gap (µm) | S. Dev. |
|---|---|---|
| 12 gsm SMS non-apertured | 115.1 | 109.7 |
| 12 gsm SMS apertured | 345.0 | 100.2 |
| 15 gsm SB non-apertured | 120.2 | 38.5 |
| 15 gsm SB apertured | 259.1 | 108.5 |

A Student's T comparison (90% confidence) was performed to determine if differences in mean values were significant. The results are provided in FIG. 13. As shown therein, separation of confidence limit ranges confirmed that the corresponding mean values were different from one another within a particular gsm weight.

In one particularly suitable embodiment, the gap between the nonwoven component 34 and the film 38 of the outer cover 32 disclosed herein is between about 200 µm and about 600 µm as determined using the test procedure disclosed herein. In one preferred embodiment, the gap between the nonwoven component 34 and the film 38 of the outer cover 32 is between about 250 µm and about 350 µm.

Adhesive Analysis

Figure 11:
FIG. 11 is a photograph showing fiberized adhesive disposed on the film of the SMS laminated control sample.

For each of the four samples, the nonwoven web was manually separated from the film. For each sample, both the nonwoven web and film were stained with osmium tetroxide and allowed to sit overnight. The adhesive used to bond the nonwoven web to the film became visible and it became evident that the adhesive was primarily adhered to the film. FIG. 11 is a photograph showing the fiberized adhesive disposed on the film taken from the control SMS laminate. FIG. 12 is a photograph showing the fiberized adhesive disposed on the film taken from apertured SMS laminate. The darker areas in the photographs correspond to the adhesive used to bond the nonwoven web and film together. The lighter gray areas correspond to adhesive located on the opposite side of the film (i.e., the side of the film facing away from the nonwoven web).

Figure 14:
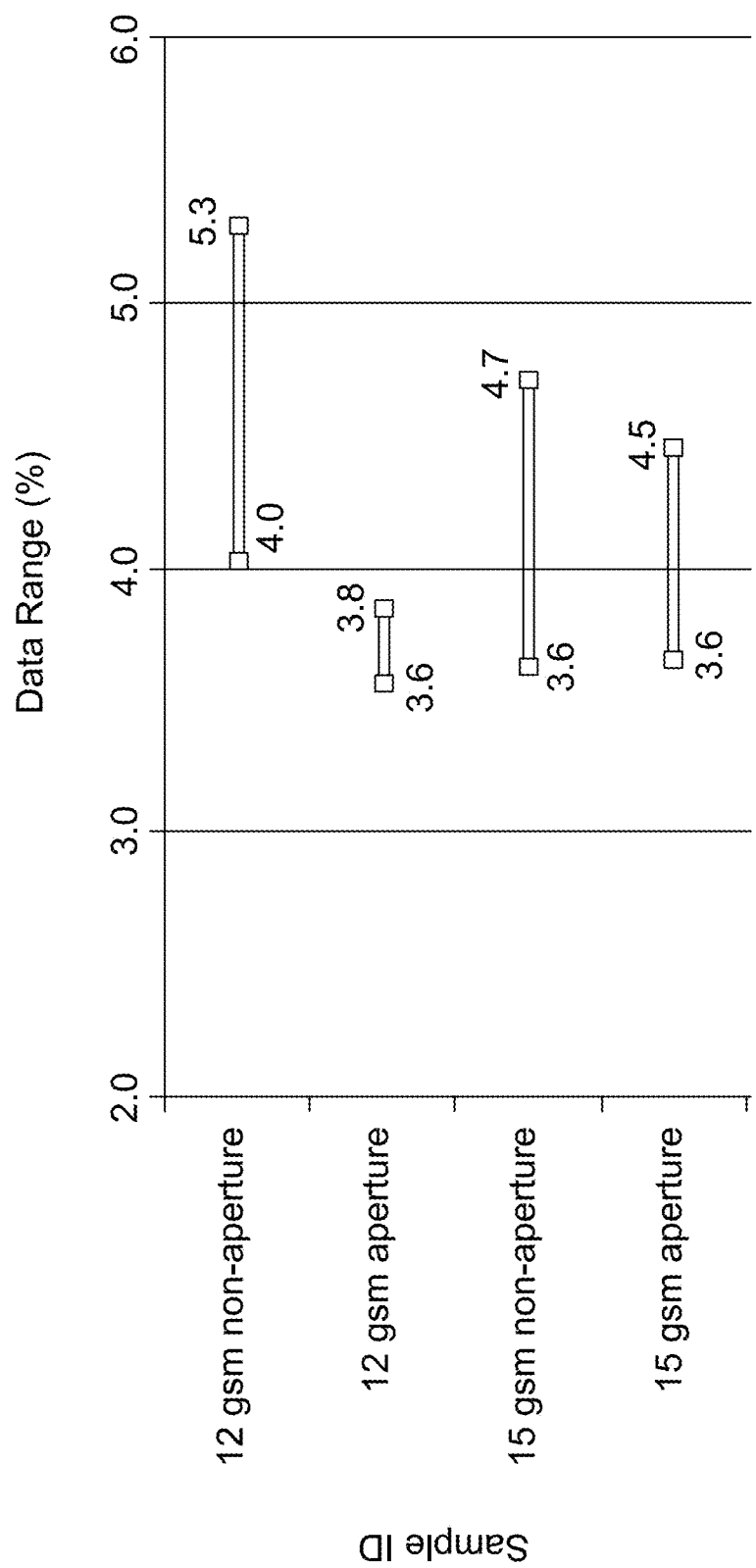
FIG. 14 is a graph illustrating a Student's T Confidence Limit Ranges for testing related to percent area coverage of the adhesive on the film.

As anticipated, the adhesive appear similar in all four of the samples. As provided in the below Table, the percent area coverage ranged from 3.7-4.7 and the width of the adhesive fibers ranged from 53.4 µm and 59.4 µm. The data appeared to be in agreement with visual observations in suggesting that little difference existed in the adhesive used in the collected samples and the aperture samples. Student's T analyses, which are provided in FIG. 14, was applied to the percent area coverage.

TABLE 3

Summary of Adhesive Analysis

| Sample ID | % Area Cover | S. Dev. | Fiber Width (µm) | S. Dev. |
|---|---|---|---|---|
| 12 gsm SMS non-apertured | 4.7 | 0.8 | 57.0 | 5.2 |
| 12 gsm SMS apertured | 3.7 | 0.2 | 53.4 | 2.5 |
| 15 gsm SB non-apertured | 4.2 | 0.7 | 59.4 | 2.6 |
| 15 gsm SB apertured | 4.1 | 0.5 | 57.0 | 3.5 |

Equivalent-Circular Diameter (ECD), Percent Open Area and Spacing Between Open Areas The aperture size (Equivalent-Circular Diameter (ECD)), percent (%) area coverage and spacing between apertures were determined for the 12 gsm SMS apertured nonwoven and the 15 gsm SB apertured nonwoven using the image analysis measurement method described herein. The image analysis measurement method determined dimensional numeric values of aperture properties using specific image analysis measurements. The method was performed using conventional optical image analysis techniques to detect apertures in the respective nonwoven and then measure a mean aperture size, % area coverage and spacing values when viewed using a camera with transmitted light illumination.

Prior to performing the image analysis measurements, each of the sample was prepared in such a way to allow isolation and visualization of a representative region of the aperture nonwoven layer only. Specifically, outer cover sample pieces were cut from a diaper using scissors into four pieces of approximately 3 inches by 3 inches in size. Ideally each piece should be cut from a separate, individual diaper product. Upon removal from the product, the nonwoven apertured layer was separated from the other outer cover layers (i.e., the film). This was done by using an organic solvent, such as hexane or chloroform, and gently peeling the adhesively bonded layers apart using forceps.

The equipment used for acquiring images of the apertured nonwoven layer included a Leica Microsystems DFC 310 camera (exposure time of 28.2 milli-seconds, gamma=1), operated in monochrome mode, and a 40-mm El-Nikkor lens (f-stop setting=4) that was fitted with a 10-mm extension tube. The lens and extension tube were attached to the camera via a standard c-mount fitting. Transmitted light illumination of the sample layer was performed using a ChromaPro 45 (Manufactured by Circle S, Tempe, Ariz.). A Prior auto-stage (Model H112) was used to place the sample on and scan by programmed movements during analysis. A Polaroid MP4 camera stand was used to attach the camera and lens to above the Prior auto-stage for imaging. The Chroma Pro 45 was located beneath the Prior auto-stage.

The image analysis software platform used to perform measurements is a QWIN Pro (Version 3.5.1) available from Leica Microsystems, having an office in Heerbrugg, Switzerland. The system and images were calibrated using a ruler with metric markings. Units of microns per pixel are used for the calibration in the QWIN Pro software. Shading correction was performed using a blank field of view illuminated by the Chroma Pro 45.

An image analysis algorithm was used to process images as well as perform measurements using Quantimet User Interactive Programming System (QUIPS) language. The image analysis algorithm is reproduced below.

```
NAME = Aperture Size, Shape, %Area & Spacing
PURPOSE = Measures aperture size, shape, % area and
  spacing
CONDITIONS = DFC 310 camera; El-Nikkor 40-mm lens
  (f/4); 10-mm-ext. tube; ChromaPro trans. light; Prior
  auto-stage; cover plate; WL = 0.95
AUTHOR = D. G. Biggs
DATE = September 19, 2013
DEFINE VARIABLES & OPEN FILES
Open File ( C:\Data\53152\Aperture Data.xls, channel
  #1 )
MFLDIMAGE = 3
TOTCOUNT = 0
TOTFIELDS = 0
IMAGE = 0
ACQOUTPUT = 0
MFRAMEH = 954
MFRAMEW = 1202
SAMPLE ID AND SET UP
Enter Results Header
File Results Header    ( channel #1 )
File Line    ( channel #1 )
PauseText    ( "Enter image file prefix name." )
Input    ( TITLE$ )
Measure frame    ( x 95,  y 84,  Width 1202,  Height
  954 )
Image frame    ( x 0,  y 0,  Width 1392,  Height 1040
  )
- Calvalue = 13.1 um/px
CALVALUE = 13.1
Calibrate    ( CALVALUE CALUNITS$ per pixel )
FRMAREA = MFRAMEH*MFRAMEW*(CALVALUE**2)
Clear Accepts
For    ( SAMPLE = 1 to 1, step 1 )
PauseText    ( "Set-up sample on the auto-stage and
  cover with light glass." )
Image Setup DC Twain   [PAUSE]   ( Camera 1,
  AutoExposure Off, Gain 0.00, ExposureTime 28.15 msec,
  Brightness 0, Lamp 38.83 )
Clear Feature Histogram #1
Clear Feature Histogram #2
Clear Feature Histogram #3
Clear Field Histogram #1
Clear Field Histogram #2
Stage    ( Define Origin )
Stage    ( Scan Pattern, 4 x 4 fields, size
  15573.000000 x 12334.000000 )
IMAGE ACQUISITION AND DETECTION - Aperture
  measurements
For    ( REPLICATE = 1 to 16, step 1 )
IMAGE = IMAGE+1
Image Setup DC Twain    ( Camera 1, AutoExposure Off,
  Gain 0.00, ExposureTime 28.15 msec, Brightness 0,
  Lamp 38.83 )
Acquire    ( into Image0 )
ACQFILE$ = "C:\Images\53152 -
  Faulks\Apertures\"+TITLE$+"_"+STR$(IMAGE)+".TIF"
Write image    ( from ACQOUTPUT into file ACQFILE$ )
Detect ( whiter than 194, from Image0 into Binary0 )
IMAGE PROCESSING
Binary Amend    ( Close from Binary0 to Binary1,
  cycles 3, operator Disc, edge erode on )
Binary Identify ( FillHoles from Binary1 to Binary2 )
PauseText    ( "Remove any detected regions not
  associated with apertures." )
Binary Edit   [PAUSE]   ( Reject from Binary2 to
  Binary3, nib Fill, width 2 )
MEASURE APERTURES
    Feature Accept :
        EquivDiam from 20. to 10000.
Measure feature    ( plane Binary3, 8 ferets, minimum
  area: 40, grey image: Image0 )
        Selected parameters: Area, X FCP, Y FCP,
        Perimeter, Roundness, EquivDiam
Feature Histogram #1    ( Y Param Number, X Param
  EquivDiam, from 20. to 20000., logarithmic, 20 bins )
Feature Histogram #2    ( Y Param Number, X Param
  Roundness, from 0.5 to 10.5, linear, 20 bins )
Feature Histogram #3    ( Y Param Area, X Param
  EquivDiam, from 20. to 20000., logarithmic, 20 bins )
Display Feature Histogram Results    ( #1, horizontal,
  differential, bins + graph (Y axis linear),
  statistics )    Data Window    ( 1242, 650, 440, 371 )
MEASURE % OPEN AREA AND SPACING
Measure field    ( plane MFLDIMAGE, into
  FLDRESULTS(4), statistics into FLDSTATS(7,4) )
        Selected parameters:   Area, Intercept H,
        Intercept V, Area%
Field Histogram #1    ( Y Param Number, X Param Area%,
  from 0. to 60., linear, 20 bins )
Display Field Histogram Results    ( #1, horizontal,
  differential, bins + graph (Y axis linear),
  statistics )    Data Window    ( 1282, 227, 414, 371 )
MEANSPACING = (FRMAREA -
  FLDRESULTS(1))/(FLDRESULTS(2)+FLDRESULTS(3))/2
Field Histogram #2    ( Y Param Number, X Param
  MEANSPACING,from 10. to 10000., logarithmic,20 bins )
Stage    ( Step, Wait until stopped + 1100 msecs )
Next    ( REPLICATE )
OUTPUT:
File    ( "Aperture ECD Histogram", channel #1 )
```

-continued

```
File Line      ( channel #1 )
File Feature Histogram Results   ( #1, differential,
statistics, bin details, channel #1 )
File Line      ( channel #1 )
File Line      ( channel #1 )
File    ( "Aperture Area-wt. ECD Histogram", channel
#1 )
File Line      ( channel #1 )
File Feature Histogram Results   ( #3, cumulative +,
statistics, bin details, channel #1 )
File Line      ( channel #1 )
File Line      ( channel #1 )
File    ( "Aperture %Area Histogram", channel #1 )
File Line      ( channel #1 )
File Field Histogram Results   ( #1, differential,
statistics, bin details, channel #1 )
File Line      ( channel #1 )
File Line      ( channel #1 )
File    ( "Mean Aperture Spacing (um)", channel #1 )
File Line      ( channel #1 )
File Field Histogram Results   ( #2, differential,
statistics, bin details, channel #1 )
Next    ( SAMPLE )
Close File   ( channel #1 )
END
```

The QUIPS algorithm was executed using the QWIN Pro software platform. The analyst was initially prompted to enter sample identification information which was sent to a designated EXCEL file to which the measurement data were also subsequently sent. The analyst was then prompted to enter an image file prefix name that was used to save the image being analyzed onto the computer hard drive.

After positioning the sample on the Prior auto-stage and ensuring it was lying flat without significant wrinkles, optimizing focus, and setting the illumination white level to approximately 0.95, the algorithm acquired an image. The analyst was then prompted to remove any detected regions not associated with apertures. Using the computer mouse in the binary edit mode, the analyst circled those detected regions that were not related to apertures. When selected, the color of the rejected area turned from green to gold. To aid in this optimizing process, the analyst toggled the 'control' and 'B' keys on the keyboard simultaneously to turn the overlying binary image on and off to assess how closely the adjusted binary matched with the boundaries of the apertures shown in the image. Once optimization was completed, only the apertures showed the binary green overlay on top of them. If a mistake was made during the editing process, the analyst simply reset to the original detected binary by clicking on the 'Undo' button located with the Binary Edit window and began the selection process again until accurate and optimal aperture selections had been made.

After optimization of detected and selected apertures, the algorithm then automatically performed measurements. Data, in histogram format, was accumulated until the algorithm had acquired and analyzed all images.

The algorithm then automatically moved the sample to the next field of view and the image acquisition and processing steps was repeated. In total, 16 images were analyzed per sample during one execution of the image analysis algorithm. When the all 16 images had acquired and analyzed, the algorithm transferred the histogram data to the EXCEL spreadsheet.

The QUIPS algorithm provided three histograms in the EXCEL spreadsheet representing equivalent circular diameter (ECD) size, % area coverage and spacing measurements for a single sample. Each histogram possessed basic statistics such as mean and standard deviation in addition to others.

As provided below in Table 4, the mean ECD of the 12 gsm apertured SMS was approximately 1 mm. The mean ECD of the 15 gsm aperture SB was approximately 0.7 mm. The mean spacing for both the 12 gsm apertured SMS and 15 gsm aperture SB was over 1 mm. The percent open area for the 12 gsm apertured SMS was approximately 13 percent and the percent open area of the 15 gsm aperture SB was approximately 7 percent.

TABLE 4

Summary of ECD size, % Area Coverage and Spacing Measurements

| Sample ID | Shape (um) | | % Open Area and Spacing | | | |
|---|---|---|---|---|---|---|
| | ECD | S. Dev. | % Area | S. Dev. | Spacing (um) | S. Dev. |
| 12 gsm SMS Apertured (Apert only) | 955.9 | 100.3 | 13.1 | 0.7 | 1131.3 | 39.5 |
| 15 gsm SB Apertured (Apert only) | 678.5 | 121.6 | 7.1 | 0.6 | 1531.5 | 75.1 |

In one particularly suitable embodiment, the nonwoven component 34 disclosed herein has a percent open area between about 5 percent and about 30 percent. More suitably, the nonwoven component 34 has a percent open area between about 8 percent and about 20 percent and, in a more preferred embodiment, a percent open area between about 10 percent and about 18 percent. As explained above, in one suitable embodiment, the apertures 70 are generally circular and have a diameter (or ERD) between about 0.5 mm and about 4 mm. As also explained above, in one suitable embodiment, each of the apertures 70 is spaced from the adjacent apertures by a distance between about 0.5 mm and about 6 mm.

Peel Strength

Each of the four samples was tested to measure the attachment strength between the nonwoven web and the film layers. The efficiency of bonding between the nonwoven web and the film of each of the laminates is determined by measuring the force required to delaminate the sample. As used herein, the "peel strength" means the average expressed in grams force that is required to separate the bonded fabric at a 180° angle over a distance of 50.8 mm (2 inches).

Each sample was prepared by cutting the sample into a specimen being 101.6±1.3 mm (4±0.05 inch) wide and 152.4±1.3 mm (6±0.05 inch) long with the long direction being parallel to the machine direction of the testing and force application. One continuous piece of masking tape having a width of 101.6 mm (4 inch) was applied to the film side of each of the samples. The tape was firmly hand smoothed to ensure an even attachment to the film. The masking tape used during the testing was commercially available from 3M of St. Paul, Minn. as product number #2307.

The specimen was then clamped by the grips of a suitable testing machine ensuring that the specimen was straight and without slack. More specifically, a free end of the nonwoven web was placed in a moving grip, and a free end of the film was placed in a stationary grip. Once the nonwoven web and film were properly secured by the respective grips, the test was run. The test parameters are provided below in Table 5.

TABLE 5

Test Parameters

| | |
|---|---|
| Crosshead Speed | 305 ± 13 mm/minute (12 ± 0.5 inch/minute) |
| Gage Length | 51 ± 1 mm (2 ± 0.05 inch) |
| Full-Scale Load | Use an appropriate load cell for the material being tested so the test value falls between 5 and 95% of the full-scale load. |
| Peel Start | 16 mm |
| Peel End | 170 mm |
| Test Endpoint | 180 mm |

The control SMS laminate had an average peel strength of 32.0 grams-force per inch (gf/in) whereas the apertured SMS laminate had an average peel strength of 28.5 gf/in. The control SB laminate had an average peel strength of 25.75 gf/in whereas the apertured SB laminate had an average peel strength of 26.75 gf/in. (See Table 6) Thus, aperturing the nonwoven web did not appear to have any significant impact on peel strength.

TABLE 6

Summary of Peel Strength

| Sample | Average Load (gf/in) |
|---|---|
| 15 gsm non-apertured SB | 25.75 |
| 15 gsm apertured SB | 26.75 |
| 12 gsm non-apertured SMS | 32.0 |
| 12 gsm apertured SMS | 28.5 |

In one particularly suitable embodiment, the peel strength of the outer cover 32 disclosed herein and, more specifically, the peel strength between the nonwoven component 34 and the film 38 is suitably between about 25 gf and about 35 gf as determined using the test procedure disclosed herein.

Kawabata Thermal Conductance

The thermal conductance of a number of nonwovens suitable for use with outer covers was evaluated from various samples using the Kawabata Evaluation System (KES) and specifically the thermal tester of the KES—Thermolabo. A description of each of the samples is provided in the following table.

TABLE 7

Sample Descriptions

| ID | Type | Code |
|---|---|---|
| Nonwoven-Korea Toray Saehan - Apertured 12 gsm SMS | Facing | Sample # 1 |
| Nonwoven-Korea Toray Saehan - Non-Apertured 12 gsm SMS | Facing | Sample # 2 |
| Nonwoven-Taejeon Inhouse - Apertured 15 gsm SB | Facing | Sample # 3 |
| Nonwoven-Taejeon Inhouse - Non-Apertured 15 gsm SB | Facing | Sample # 4 |
| Nonwoven-Toray Saehan - Apertured 15 gsm SB | Facing | Sample # 5 |
| Nonwoven-China Toray Saehan - Apertured 15 gsm SB | Facing | Sample # 6 |
| Nonwoven-China Hejie - Apertured 13 gsm SMS | Facing | Sample # 7 |

The Thermolabo of the KES is used to measure the heat and moisture transfer properties of materials. The key components of the Thermolabo are two heated plates of 10 cm×10 cm and 5 cm×5 cm. The small heated plate of 5 cm×5 cm is used to measure the thermal conductance of a material when convective heat loss is absent. The heat loss in watts from the small plate is measured when the sample is sandwiched between the small heated plate maintained at 35° C. and a test surface maintained at 20° C. The result is expressed as $W/m^{2\circ}$ C. Higher thermal conductance values indicate higher heat conduction.

The thermal conductance values of the dry nonwovens were measured using the Thermolabo of the KES. The conduction properties of the nonwovens were different. As seen in Table 8 below, five groupings were generated with the following order sample 2 (Non-Apertured 12 gsm SMS) >>sample 4 (Non-Apertured 15 gsm SB)>>sample 1 (Apertured 12 gsm SMS)>sample 6 (China Apertured 15 gsm SB)>>sample 3 (Taejeon Apertured 15 gsm SB)>>sample 5 (Apertured 15 gsm SB)>sample 7 (Apertured 13 gsm SMS). The trend is clear that the non-apertured nonwovens have a higher heat conduction ability than the apertured nonwovens. It is believed that the holes in the aperture facing provide good insulation.

TABLE 8

Result of the Conductance Testing

| Level | | | | | Conductance $W/m^2$ ° C. |
|---|---|---|---|---|---|
| Sample # 2 | A | | | | 158.9 |
| Sample # 4 | | B | | | 132.7 |
| Sample # 1 | | | C | | 92.9 |
| Sample # 6 | | | C | D | 85.5 |
| Sample # 3 | | | | D | E | 78.2 |
| Sample # 5 | | | | | E | 73.4 |
| Sample # 7 | | | | | E | 70.3 |

Levels not connected by same letter are significantly different.

In one suitable embodiment, the nonwoven component 34 of the outer cover 32 disclosed herein has a conductance between about 70 $W/m^{2\circ}$ C. and about 100 $W/m^{2\circ}$ C. as determined using the test procedure disclosed herein. In one preferred embodiment, the nonwoven component 34 has a conductance between about 80 $W/m^{2\circ}$ C. and about 90 $W/m^{2\circ}$ C. as determined using the test procedure disclosed herein.

Kawabata Compression Strain

The Compression Strain (EMC) of the nonwonvens listed in Table 7 was tested using the KES and the results are provided in Table 9. As set forth in the equations below, the compression Rate measures the percentage of the thickness change between two pressure levels i.e. 0.5 $gf/cm^2$ and 50 $gf/cm^2$. Higher values of EMC indicate that the samples have higher compressibility and cushioning.

$EMC=(T_0-T_n)/T_0 \times 100$ where
T=Thickness of specimen, cm
$T_0$=Thickness of specimen at pressure 0.5 $gf/cm^2$, cm
$T_n$=Thickness of specimen at pressure 50 $gf/cm^2$, cm

TABLE 9

Results of the EMC Testing

| Level | | EMC |
|---|---|---|
| Sample # 3 | A | 78.5 |
| Sample # 5 | A | 75.8 |
| Sample # 1 | A | 75.4 |

TABLE 9-continued

Results of the EMC Testing

| Level | | | EMC |
|---|---|---|---|
| Sample # 7 | A | B | 74.6 |
| Sample # 6 | | B | 69.3 |
| Sample # 2 | | C | 50.9 |
| Sample # 4 | | C | 46.7 |

Levels not connected by same letter are significantly different

In one suitable embodiment, the nonwoven component 34 of the outer cover 32 disclosed herein has an EMC value between about 60 and about 90 as determined using the test procedure disclosed herein. In one preferred embodiment, the nonwoven component 34 has an EMC value between about 70 and about 80 as determined using the test procedure disclosed herein.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An outer cover for an absorbent article, the outer cover comprising a fibrous nonwoven component having a plurality of apertures formed therein and a breathable film bonded to the apertured nonwoven component, the apertures in the nonwoven component being formed by needling prior to the film being bonded to the nonwoven component such that the nonwoven component is bonded to the film at locations adjacent the apertures forming a plurality of domed areas extending away from the film such that a gap is formed between the nonwoven component and the film, the apertures having a minimum width adjacent to the film and a maximum width adjacent to an outer extent of the nonwoven component, the film being free of a plurality of apertures, the nonwoven component having a conductance between 70 W/m$^{2\circ}$ C. and 100 W/m$^{2\circ}$ C., and the gap between the nonwoven component and the film being between 200 and 400 µm.

2. The outer cover set forth in claim 1 wherein the film is adhesively bonded to the apertured nonwoven.

3. The outer cover set forth in claim 1 wherein at least some of the apertures of the plurality of apertures have a minimum width between 0.5 mm and 4.0 mm.

4. The outer cover set forth in claim 1 wherein each of the apertures of the plurality of apertures is spaced from adjacent apertures by a distance between 0.5 mm and 6 mm.

5. The outer cover set forth in claim 1 wherein the plurality of apertures define an aperture density between 9 per square centimeter and 36 per square centimeter.

6. The outer cover set forth in claim 5 wherein the plurality of apertures define an aperture density of approximately 18 apertures per square centimeter.

7. The outer cover set forth in claim 1 wherein the ratio of the maximum width to the minimum width is 1.5.

8. The outer cover set forth in claim 1 wherein at least some of the apertures of the plurality of apertures are readily visible to the user.

9. An absorbent article comprising the outer cover set forth in claim 1.

10. An outer cover for an absorbent article, the outer cover comprising a fibrous nonwoven component having a plurality of apertures formed therein and a breathable film bonded to the apertured nonwoven component, the apertures in the nonwoven component being formed such that the nonwoven component is bonded to the film at locations adjacent the apertures forming a plurality of domed areas extending away from the film such that a gap is formed between the nonwoven component and the film, the apertures having a minimum width adjacent to the film and a maximum width adjacent to an outer extent of the nonwoven component, the nonwoven component having a conductance between 70 W/m$^{2\circ}$ C. and 100 W/m$^{2\circ}$ C., and the gap between the nonwoven component and the film being between 200 and 400 µm, and the outer cover having a breathability between 1,500 grams/m$^2$-24 hours and 10,000 grams/m$^2$-24 hours as determined by the WVTR test procedure.

11. The outer cover set forth in claim 10 wherein the outer cover has a breathability between 2,500 grams/m$^2$-24 hours and 7,000 grams/m$^2$-24 hours as determined by the WVTR test procedure.

12. The outer cover set forth in claim 11 wherein the outer cover has a breathability between 3,500 grams/m$^2$-24 hours and 5,000 grams/m$^2$-24 hours as determined by the WVTR test procedure.

13. The outer cover set forth in claim 12 wherein the outer cover has a breathability of 4,000 grams/m$^2$-24 hours as determined by the WVTR test procedure.

14. An outer cover for an absorbent article, the outer cover comprising a fibrous nonwoven component having a plurality of apertures formed therein and a breathable film bonded to the apertured nonwoven component, the apertures in the nonwoven component being formed such that the nonwoven component is bonded to the film at locations adjacent the apertures forming a plurality of domed areas extending away from the film such that a gap is formed between the nonwoven component and the film, the apertures having a minimum width adjacent to the film and a maximum width adjacent to an outer extent of the nonwoven component, the nonwoven component having a conductance between 70 W/m$^{2\circ}$ C. and 100 W/m$^{2\circ}$ C., and the gap between the nonwoven component and the film being between 200 and 400 µm, and the outer cover having a peel strength between the nonwoven component and the film between 25 gf and 35 gf.

15. The outer cover set forth in claim 14 wherein the nonwoven component has an EMC value between 60 and 90.

16. The outer cover set forth in claim 15 wherein the nonwoven component has an EMC value between 70 and 80.

\* \* \* \* \*